US007655406B2

(12) United States Patent
Wychowski et al.

(10) Patent No.: US 7,655,406 B2

(45) Date of Patent: *Feb. 2, 2010

(54) NUCLEOTIDE SEQUENCES CODING FOR THE NON-STRUCTURAL PROTEINS OF THE HEPATITIS C VIRUS

(75) Inventors: Czeslaw Wychowski, Meurchin (FR); Gilles Duverlie, Amiens (FR); Jean Dubuisson, Faches-Thumesnil (FR); Andre Pillez, Lille (FR)

(73) Assignee: Centre National de la Recherche Scientifique, Paris (FR)

(*) Notice: Subject to any disclaimer, the term of this patent is extended or adjusted under 35 U.S.C. 154(b) by 0 days.

This patent is subject to a terminal disclaimer.

(21) Appl. No.: 11/865,954

(22) Filed: Oct. 2, 2007

(65) Prior Publication Data

US 2008/0220410 A1 Sep. 11, 2008

Related U.S. Application Data

(62) Division of application No. 10/475,989, filed as application No. PCT/FR02/01422 on Apr. 25, 2002, now Pat. No. 7,314,710.

(30) Foreign Application Priority Data

Apr. 27, 2001 (FR) .................................. 01/05732

(51) Int. Cl.

| | |
|---|---|
| ***C12Q 1/70*** | (2006.01) |
| ***C12Q 1/68*** | (2006.01) |
| ***C12N 15/09*** | (2006.01) |
| ***C12N 15/51*** | (2006.01) |
| ***C07H 21/00*** | (2006.01) |

(52) U.S. Cl. .............................. 435/6; 435/5; 435/69.1; 435/325; 435/354; 435/320.1; 536/23.2; 536/23.72

(58) Field of Classification Search ....................... None
See application file for complete search history.

(56) References Cited

U.S. PATENT DOCUMENTS

| | | | | |
|---|---|---|---|---|
| 5,571,712 | A | 11/1996 | Haynes et al. | |
| 5,998,174 | A | 12/1999 | Glorioso et al. | |
| 6,127,116 | A | 10/2000 | Rice et al. | |
| 6,153,421 | A | 11/2000 | Yanagi et al. | |
| 6,159,939 | A | 12/2000 | Glenn | |
| 6,630,343 | B1 * | 10/2003 | Bartenschlager | 435/320.1 |
| 7,314,710 | B2 * | 1/2008 | Wychowski et al. | 435/5 |
| 2004/0234506 | A1 | 11/2004 | Jin et al. | |

FOREIGN PATENT DOCUMENTS

| | | |
|---|---|---|
| WO | WO 94/25064 | 11/1994 |
| WO | WO 96/24662 | 8/1996 |

OTHER PUBLICATIONS

Definition "virus", Online Medical Dictionary, cancerweb.ncl.ac.uk/omd/, 2009.*

Valli M B et al.: Hepatitis C Virus Infection of a Vero Cell Clone Displaying Efficient Virus-Cell Binding Research in Virology, Elsevier, Paris, FR., vol. 148, No. 2, Mar. 1997, pp. 181-186, XP000878532 ISSN: 0923-2516.

Germi R et al:"Hepatitis C virus adsorption step study on different cell lines.", Travaux Scientifiques Des Chercheurs Du Service De Sante Des Armees, No. 20,pp. 55-56, XP001042364, ISSN: 0243-7473 1999.

Germi R et al.: "Les systemes de culture du virus de 1' hepatite C.", Pathologie Biologie, vol. 49, No. 3, Apr. 2001. pp. 255-261, XP001042317, ISSN: 0369-8114.

Bartenschlager Ralf et al.: "Replication of hepatitis C virus.", Journal of General Virology, vol. 81, No. 7, Jul. 2000, pp. 1631-1648, XP002186769 ISSN: 0022-1317.

Pietschmann et al., "Persistent and transient replication of full-length hepatitis C virus genomes in cell culture," Journal of Virology, vol. 76, No. 8, pp. 4008-4021 (Apr. 2002).

Bowie et al., "Deciphering the Message in Protein Sequences: Tolerance to Amino Acid Substitutions," Science, vol. 247, No. 4948, pp. 1306-1310 (Mar. 1990).

Frese et al., "Human MxA Protein Inhibits Tick-Borne Thogo Virus but Not Dhori Virus," Journal of Virology, vol. 69, No. 6, pp. 3904-3909 (Jun. 1995).

Heller et al., "An in vitro model of hepatitis C virion production," Proc. Of the Natl. Acad. Of Sci., USA, vol. 102, No. 7, pp. 2579-2583 (Feb. 2005).

Lohmann et al., "Replication of Subgenomic Hepatitis C Virus RNAs in a Hepatoma Cell Line," Science, vol. 285, No. 5424, pp. 110-113 (Jul. 1999).

Bartenschlager et al., "Replication of the hepatitis C virus in cell culture," Antiviral Research, vol. 60, No. 2, pp. 91-102 (Oct. 2003).

Bartenschlager, "The hepatitis C replicon system: From basic research to clinical application," J. of Hepatology, vol. 43, No. 2, pp. 210-216 (Aug. 2005).

Bartenschlager, "Hepatitis C virus replicons: potential role for drug development," Drug Discovery, vol. 1, No. 11, pp. 911-916 (Nov. 2002).

Bonte et al., "Positive effect of the hepatitis C virus nonstructural 5A protein on viral multiplication," Archives of Virology, vol. 149, No. 7, pp. 1353-1371 (Jul. 2004).

* cited by examiner

*Primary Examiner*—Zachariah Lucas
(74) *Attorney, Agent, or Firm*—Young & Thompson

(57) ABSTRACT

The invention concerns the use of cells capable of carrying out a process of prenylation of proteins coded by the hepatitis C virus (HCV) genome, such as prenylation of the NS5A protein, for replicating and, if required, the production of HCV or derivative viable mutants, in a suitable culture medium.

4 Claims, 3 Drawing Sheets

NUCLEOTIDE SEQUENCES CODING FOR THE NON-STRUCTURAL PROTEINS OF THE HEPATITIS C VIRUS

This application is divisional application of U.S. patent application Ser. No. 10/475,989, filed Mar. 9, 2004 now U.S. Pat. No. 7,314,710, which is a national stage of International Application PCT/FR02/01422 filed Apr. 25, 2002.

The invention relates to a process for replicating the hepatitis C virus. The invention also relates to a process for screening inhibitors of the hepatitis C virus.

The hepatitis C virus or HCV, identified in 1989 by Choo's team (Choo et al., 1989), is the major agent of the viral infections that have for long been called non-A non-B hepatitides. The term "non-A non-B" was introduced in the 70s to describe hepatitides of which the etiological agents, not yet identified, appear serologically different from hepatitides A and B, thanks to the introduction of immunological tests (Feinstone et al., 1975; Prince et al., 1974).

In clinical terms, infection by the hepatitis C virus is characterized by a strong predominance of the asymptomatic forms and the frequency of the evolution towards chronicity.

The molecular cloning and the sequencing of the hepatitis C virus were initially carried out by Choo et al. (1988 and 1989) and confirmed by other teams (Kato et al., 1990; Okamoto et al., 1992; Inchauspé et al., 1991). The sequential analysis of the genome of the HCV reveals an single open reading frame of which the AUG initiator is found in position 342 of the genome. As with certain positive-RNA viruses, the non-coding 5' region of the HCV is involved in the process of initiation of the translation by the presence of an internal ribosomes entry site or IRES (Tsukiyama-Kohara et al., 1992; Reynolds et al., 1995).

The construction of a cDNA coding for all of the polyprotein of the hepatitis C virus, and its expression in various procaryotic or eucaryotic vectors, have allowed the organization of the genome to be defined, and the various proteins arising from the maturation of the polyprotein to be characterized. Different processes for cleaving this polyprotein, involving viral and cell proteases, generate the structural and non-structural proteins. Studies of in vitro translation and in vivo expression (Grakoui et al., 1993; Hijikata et al., 1991) have allowed the order in which the proteins are coded by the genome to be established, and this is schematicized as follows: $H_2N$—C-$E_1$-$E_2$-p7-NS2-NS3-NS4A-NS4B-NS5A-NS5B-COOH.

The first third of the genome of hepatitis C codes for the structural proteins C, E1, E2 and p7. The different proteins of the structural region are the result of the involvement of proteases of cellular origin.

The C protein, which has a molecular weight of approximately 21 kDa, and contains 173 amino acids, is the capsid protein. This protein is the principal constituent of the nucleocapsid of the HCV. The carboxy-terminal region located between the amino acids 174 to 191 constitutes the signal peptide of the E1 glycoprotein. This sequence is cleaved by a signalase. Capsid protein C, of very basic composition, because of its richness in amino acids arginine and lysine (23.5% of the amino acids in the N-terminal region) could be involved in the RNA-proteins interactions.

The E1 and E2 glycoproteins, which have respective molecular weights of 31 and 70 kDa, constitute the envelope glycoproteins. They are type I membranous glycoproteins, each having a hydrophobic domain at their carboxy-terminal end. Moreover, they each have a hydrophobic signal sequence at the N-terminal end allowing a translocation in the endoplasmic reticulum and a maturation of these proteins by cell signalases. The amino acids contained between 174-191 and the amino acids contained between 371-383 of the polyprotein of the HCV correspond to the signal peptides of the E1 and E2 glycoproteins. The last amino acid of the sequence of E2 is situated in position 746 of the polyprotein of the HCV and the last amino acid of the E1 glycoprotein is in position 383 of the polyprotein, which means that the signal peptide of the E2 glycoprotein is an integral part of E1.

Between E2 and the NS2 protein, a small protein p7 has been identified, the function of which is still unknown.

The remaining two thirds of the genome of the HCV code for the non-structural proteins NS2, NS3, NS4A, NS4B, NS5A and NS5B.

The NS2 protein is a hydrophobic protein of 23 kDa, the N-terminal amino acid of which is in position 810 and the C-terminal amino acid in position 1026 on the polyprotein. The NS2 protein and the N-terminal third of NS3 would act as a protease ensuring the cleavage between the NS2 and NS3 proteins (Grakoui et al., 1993). This protease would be a zinc-dependent metallo-protease. This observation is based on the fact that the activity of this protein would be inhibited by EDTA and stimulated by $ZnCl_2$. The histidine in position 952 and the cysteine in position 993 seem to be involved in the catalytic activity of this enzyme.

The NS3 protein is a protein of 70 kDa. Located between the amino acids 1027 and 1657 of the polyprotein of the HCV, it has two separate functional domains: the N-terminal part of the protein codes for a protease and the C-terminal domain for a RNA-dependent NTPase/helicase.

The NS4 protein is a protein which has an apparent molecular weight of 8 kDa. It is located on the polyprotein between the amino acids 1658 and 1711. Its function would be to act as cofactor for the NS3 protease, as studies have shown that the cleavage of the junctions NS3/NS4A, NS4A/NS4B and NS4B/NS5A requires the NS4A protein. This protein, without being indispensable, also accelerates the NS5A/NS5B cleavage.

The NS4B protein of the HCV, which has a molecular weight of 27 kDa, does not have a function that is known to date. The NS4 B protein is located between the amino acids 1712 and 1972 of the polyprotein of the HCV. Moreover the NS4B protein appears as a basic protein.

The NS5A protein of the HCV, which has a molecular weight of 56 kDa, is a protein which interacts with the NS5B protein and probably participates in the replication of the HCV. The NS5A protein is located between the amino acids 1973 and 2420 of the polyprotein of the HCV of the genotype 1a. However, according to the different genotypes observed, this protein can comprise different insertions by way of amino acids: thus it comprises 466 amino acids for the genotype 2a, 452 amino acids for the genotype 3a whereas it comprises only 466 amino acids for the genotype 1a. Although the principal function of this protein is still unknown, it nevertheless displays some characteristics. Thus the expression of a 56 kDa protein and of a 58 kDa protein has been observed. It corresponds to a phosphorylation and to a hyperphosphorylation of the NS5A protein leading respectively to the production of the 56 and 58 kDa proteins.

The NS5B protein which has a molecular weight of 68 kDa is positioned between the amino acids 2421 and 3011 of the polyprotein. The presence of Gly-Asp-Asp peptide units or GDD unit, analogous to those found in the polypeptide sequence of the RNA-dependent RNA polymerases of numerous RNA viruses, allows the NS5B protein to be proposed as a candidate for the function of replicase.

The hepatitis C virus seems to express its pathogenic power exclusively in the liver of the infected patients or animals (Negro et al., 1992). However, attempts at viral propagation on human hepatocytes or originating in chimpanzees have resulted in abortive cycles (Lanford et al., 1994). Other work reported by Seipp et al. (1997), and relating to the infection of different cell lines (HuH7 and HepG2) or cells of porcine origin (PK15) have revealed the possibility of a viral infection and of a replication. It is difficult at present to envisage the exploitation of these cell systems with a view to a mass viral production. The replication of the viral genome in the lymphocytes of the peripheral blood of patients suffering from hepatitis C, or in a sub-population of monocytes/macrophages of PBMC (peripheral blood mononuclear cells) has been described by different authors (Bouffard et al., 1992). But, more recently, Shimizu and his collaborators (Shimizu et al., 1992; Shimizu et al., 1994) have shown that the replication of the HCV was able to take place either in a line originating in a lymphoblastic T-cell leukemia (Molt4 cells) or in a HPB-Ma cell line previously infected by a murine retrovirus (murine leukaemia virus). An infectious cycle has also been reproduced in these latter cells. The capacity of these cells to be able to replicate the viral genome of the HCV has allowed the introduction of an in vitro neutralization test (Shimizu et al., 1994). Therefore the neutralization of the virus after incubation with certain sera of patients has been correlated with the loss of the power of replication of the HCV on these cell lines. Moreover, in using the HPB-Ma cell line, the authors were also able to show the reinfection of the cells by the HCV and the sensitivity of the virus to interferon (Shimizu et al., 1994).

Besides, it has been shown recently by the groups of C. M. Rice (Kolykhalov et al., 1997) and of R. H. Purcell (Yanagi et al., 1997) that it is possible to reconstitute an infectious cDNA of the HCV. In fact, chimpanzees that had received an intrahepatic injection of RNA transcribed from the complete cDNA of the HCV were capable of reproducing an infection after a few weeks.

European patent application EP 1 043 399 relates to a system for the cell culture of the hepatitis C virus, which principally comprises eukaryotic cells containing a genetic material specific to the transfected HCV, characterized by the fact that the eukaryotic cells are cells of human hepatomas and that the genetic material specific to the transfected HCV is an RNA construction of the HCV, which comprises the RNA segments specific to the HCV: 5'NTR, NS3, NS4A, NS4B, NS5A, NS5B and 3'NTR as well as an additional "marker" selection gene (selection gene). The cells in question are HuH7 cells of human hepatomas and the genotype of the hepatitis C virus used is the genotype 1b (Lohmann et al., 1997). However, this replication process is not applicable to the genotype 1a of the HCV.

The major problem with the study of the hepatitis C virus (HCV) is the absence of a cell system capable of reproducing the viral cycle of the HCV. In fact, it is difficult at present to produce any hypotheses in order to explain the reason for this. However, the possibility of the hepatitis C virus to replicate itself on certain cell lines has sometimes been mentioned (Kato and Shimotohno, 2000). The result is that all the knowledge acquired concerning the hepatitis C virus, in particular about its structure, the assembly of its proteins and its genomic organization, rests on studies of complementary DNA translation of the HCV carried out in vitro in an acellular system and in vivo in the cells in culture. Thus, the mechanisms of the propagation and of the viral replication are little known. Blockages may occur at different molecular levels. They can take place at the level of the adsorption of the viral particle and of its receptor, of the decapsidation of the viral particle, of the expression of the genome or of the replication.

Thus, one of the aspects of the invention is the use of cells which present particular cell factors, permitting the replication of the genome of the hepatitis C virus in these cells.

One of the other aspects of the invention is the use of these cells for replication as well as multiplication and therefore the production of the hepatitis C virus.

One of the other aspects of the invention is to provide a novel process for the replication and the production of the genotype 1a of the hepatitis C virus by transformation of suitable cells.

One of the other aspects of the invention is to provide a novel screening process for anti-HCV agents and thus to provide inhibitors of the hepatitis C virus.

The invention relates to the use of cells capable of carrying out a prenylation process for proteins coded by the genome of the hepatitis C virus (HCV), such as the prenylation of the NS5A protein, for the replication and, where applicable, the production of the HCV or of derived viable mutants, in a suitable culture medium.

Numerous proteins of cellular, but also viral, origin undergo post-translational modifications which orient their cell location. Some of these proteins thus bear modifications of fatty acids. A particularly interesting modification is prenylation which corresponds to the alkylation of a cysteine by a farnesyl (15 carbon atoms) or geranylgeranyl (20 carbon atoms) group, these groups resulting from the polymerization of mevalonic acid.

The presence of two cysteine residues (CC) at the carboxy-terminal end of the NS5A protein (Grakoui et al., 1993) indicates that this protein can be modified by prenylation (Casey P. J., 1992). The prenyltransferases can add to the cysteine in C-terminal position a farnesyl or geranylgeranyl group of 15 to 20 carbon atoms, respectively, and which derive from the polymerization of mevalonic acid. The units identified and responsible for these modifications are often of CAAX or CC type, where C is cysteine, A is an aliphatic amino acid and X is an amino acid such as M (methionine), S (serine), Q (glutamine) or L (leucine).

The expression "replication of the HCV" designates the molecular process or processes leading to the synthesis of a strand of negative polarity which will serve to engender new strands of positive polarity constituting the genomic material of the HCV.

The expression "production of the HCV" describes the possibility for a given cell to reproduce infectious particles of the hepatitis C virus (viral multiplication cycle).

The expression "derived viable mutants" designates viable variants that can originate only in the selection of the replicon of the HCV under different selection pressures. This selection pressure must engender the selection of mutations in the genome of the HCV which lead to a better replication, to a more quantitative expression of the different proteins and as a result to a better resistance of the cells vis-à-vis the selection product. Only viable mutations permitting resistance to the selection pressure are observed. The other, non viable, mutations, lead to the death of the cell.

The expression "in a suitable culture medium" describes the medium in which the cell line is best able to grow. The culture medium can be in particular the DMEM/10% FCS (foetal calf serum) medium supplemented by the elements necessary for selection, for example neomycin (G418) or hygromycin B.

An advantageous use of the invention is the use, as defined above, of cells of mammals, in particular of monkey kidney cells, also called Vero cells.

Vero cells are cells of normal kidneys originating from African green monkeys (*Cercopithecus aethiops*, ATCC: CCL81)

The invention also relates to the use as defined above of Vero cells transformed by a resistance gene to an antibiotic, such as neomycin, in particular Vero/G418 cells.

According to an advantageous embodiment of the invention, the cells used originate from the particular cell line Vn5, resulting from the transformation of a Vero cell by the resistance gene to an antibiotic, such as neomycin. These Vn5 or Vero/G418 cells are described by Frese et al. (1995).

According to an advantageous embodiment of the invention, the antibiotic resistance gene can be chosen from the bleomycin, phleomycin, zeocin or puromycin resistance genes.

The invention relates to the use as defined above of cells, such as Vero cells, transformed where applicable by a resistance gene to an antibiotic, such as neomycin, said cells being transformed by a nucleic acid containing all or part of the genome of the HCV or by mutants derived from the HCV.

According to an advantageous embodiment of the invention, the Vero cells can be transformed by resistance genes to the following antibiotics: bleomycin, phleomycin or zeocin resistance genes; or puromycin, hygromycin B or neomycin resistance genes.

In order to transform the cells, and in particular the Vero/G418 cells, the ribonucleic acid used comprises the following parts of the genome of the HCV: the non-coding 5' and 3' regions, a part of the sequences coding for the capsid protein C (sequence comprised between 50 and 100 nucleotides) and the region coding for the non-structural proteins, namely NS2, NS3, NS4A, NS4B, NS5A and NS5B or NS3, NS4A, NS4B, NS5A and NS5B.

The viable variants of the HCV advantageously result from the selection of the replicon under different selection pressures. This pressure then causes the selection of mutations in the genome which lead to a better resistance against the selection product.

The invention also relates to the use as defined above, characterized in that the nucleic acid is chosen from:

- those coding for the structural and non-structural proteins of the HCV or
- those coding for the non-structural proteins of the HCV or
- the replicons containing a resistance gene to an antibiotic, in particular hygromycin B, and a nucleotide sequence coding for the non-structural proteins of the HCV.

A nucleic acid coding for the structural and non-structural proteins of the HCV is for example the nucleotide sequence SEQ ID NO: 2.

A nucleic acid coding for the non-structural proteins of the HCV is for example the nucleotide sequence SEQ ID NO: 1.

Among the structural proteins of the HCV are included the proteins as mentioned above, namely the C, E1, E2 and p7 proteins.

Among the non-structural proteins of the HCV are included the NS2, NS3, NS4A, NS4B, NS5A and NS5B proteins.

The expression "replicon containing a resistance gene to an antibiotic, in particular hygromycin B, and a nucleotide sequence coding for the non-structural proteins of the HCV" designates a nucleic acid containing the non-coding 5' and 3' regions of the genome of the HCV, a part of the sequence coding for the capsid protein C of the HCV followed by the nucleotide sequences coding for hygromycin-B-phosphotransferase (HPH) and nucleotide sequences coding for the NS2, NS3, NS4A, NS4B, NS5A and NS5B proteins, defined above (see FIG. 1).

The possibility of replacing all or part of the structure proteins having been realized for other positive-RNA viruses and currently in possession of a complete cDNA of the HCV, a replicon of the HCV was constructed keeping a part of the sequences coding for the capsid protein C. In fact, it was shown by Dr Jackson's team (Reynolds et al., 1995) that these sequences played an important part in the initiation of the translation of the HCV via the IRES (internal ribosomes entry site). In order to maintain the integrity of this IRES and under the conditions of the HCV, a part of the sequences coding for the capsid protein was preserved. The sequence of the structure proteins was thus substituted by the sequence coding for the hygromycin B resistance gene. Through this approach, it is possible to keep the cells under hygromycin B selection pressure in order to select resistant cell clones. These results can be explained only by the maintenance of the replicon inside the cell. However, other selection markers can be used in order to facilitate this selection, such as puromycin, zeocin or bleomycin.

The invention relates to the use as defined above, characterized in that the cells are transformed by a nucleic acid chosen from the nucleotide sequences SEQ ID NO: 1, SEQ ID NO: 2 and SEQ ID NO: 3.

The sequence SEQ ID NO: 1 corresponds to the part of the sequence of the HCV of genotype 1a coding for the non-structural proteins, namely the NS2, NS3, NS4A, NS4B, NS5A and NS5B proteins.

The sequence SEQ ID NO: 2 corresponds to the entire sequence of the HCV of genotype 1a (structural and non-structural proteins).

The sequence SEQ ID NO: 3 corresponds to the replicon obtained by fusion of a hygromycin B resistance gene with the part of the sequence of the HCV of genotype 1a coding for the non-structural proteins.

The invention relates to the use as defined above for the replication and, where applicable, for the production of the HCV of type 1a.

The type 1a genotype of the HCV is in particular described by Peter Simmonds (2001).

The principal characteristic of the HCV genotypes is their variability. In fact, the genomes differ among themselves by virtue of their nucleotides with a percentage varying from 31 to 34%, which also means a variability for amino acids.

The invention relates to the use as defined above of cells as deposited at the CNCM on the 13 of Apr. 2001 under the numbers I-2658 and I-2659.

The strain registered under the number I-2659 corresponds to the Vero/G418 (Vn5) cells, as defined above.

The strain registered under the number I-2658 corresponds to Vero/G418+ replicon cells, which are Vero/G418 cells in which the sequence SEQ ID NO: 3 as defined above has been inserted.

The invention relates to a nucleotide sequence characterized in that it comprises or is constituted by SEQ ID NO: 1.

The invention relates to a nucleotide sequence characterized in that it comprises or is constituted by SEQ ID NO: 3.

The invention relates to a recombinant vector, in particular plasmid, cosmid, phage or virus DNA, containing a nucleotide sequence as defined above.

An advantageous vector of the invention is a recombinant vector as defined above, containing the elements necessary for the expression in a host cell of the polypeptides encoded by the nucleic acids as defined above, inserted into said vector.

According to an advantageous embodiment of the invention, the recombinant vector defined above contains in particular a promoter recognized by the RNA polymerase of the host cell, in particular an inducible promoter and optionally a transcription, termination sequence, and optionally a signal and/or anchorage sequence.

According to another advantageous embodiment of the invention, the recombinant vector, as defined above, contains the elements which permit the expression of a nucleotide sequence, as defined above, as a mature protein or a fusion protein.

According to an advantageous embodiment of the invention, the vector used for the cloning of the HCV is the pGEM 3Zf (+) vector (Promega). This vector contains the ampicillin resistance gene, the replication origin of the plasmid and the intergenic fragment of the phage f1. Moreover, the fragments of the HCV are placed under the control of the T7 or SP6 promoter.

The invention also relates to a host cell, chosen in particular from bacteria, viruses, yeasts, fungi, plants or mammalian cells, said host cell being transformed, in particular using a recombinant vector as defined above.

According to an advantageous embodiment of the invention, the host cell as defined above contains the regulating elements permitting the expression of one of the nucleotide sequences as defined above.

According to an advantageous embodiment of the invention, the DH5 α bacteria, marketed by the company Gifco, are used. These bacteria are used to amplify, after transfection, the pGEM3Zf plasmids (Promega) which possess the complementary sequences of the HCV or the sequences of the replicon. All the plasmids containing sequences of the HCV are used for the transformation of the DH5α bacteria. The sequences of the HCV are stables in this bacterium.

According to an advantageous embodiment of the invention, the cells used for the viral production of the recombinant vaccine viruses are in particular the Tk—(see experimental part, I-3) or the CV1L cells.

The recombinant vaccine viruses are produced from pTM1 plasmids (Moss et al., 1990) and recombined according to the experimental procedure. These recombinant viruses contain the sequences coding for the NS5A protein or forms truncated in the N-terminal part of the NS5A protein.

The CV1 cell strain is a continuous line derived from cells of African green monkey kidneys (AGMK) and the CV1-L strain results from a sub-cloning of the CV1 strain.

The invention relates to any transformed cell constituted by a Vero/G418 cell, comprising a nucleic acid selected from:

- those coding for the structural and non-structural proteins of the HCV or
- those coding for the non-structural proteins of the HCV or
- the replicons containing a resistance gene to an antibiotic, in particular hygromycin B, and a nucleotide sequence coding for the non-structural proteins of the HCV.

An advantageous cell according to the invention is a cell as defined above, constituted by a Vero/G418 cell comprising a replicon constituted by a nucleic acid chosen from those containing a resistance gene to an antibiotic, such as hygromycin B, and a nucleotide sequence coding for the non-structural proteins of the HCV, namely NS2, NS3, NS4A, NS4B, NS5A and NS5B.

An advantageous cell of the invention is a cell as defined above, such as the Vero/G418 cell deposited at the Collection Nationale de Cultures de Microorganisms (CNCM), Institut Pasteur, 25, rue de Docteur Roux, 75724, Paris cedex 15, France on the 13 of Apr. 2001 under the number I-2659.

An advantageous cell according to the invention is a cell as defined above, such as the Vero/G418 cell, comprising a nucleic acid containing a resistance gene to an antibiotic, such as hygromycin B, and a nucleotide sequence coding for the non-structural proteins of the HCV, and deposited at the Collection Nationale de Cultures de Microorganisms (CNCM), Institut Pasteur, 25, rue de Docteur Roux, 75724, Paris cedex 15, France on the 13 of Apr. 2001 under the number I-2658.

An advantageous cell according to the invention is a cell as defined above, constituted by a Vero/G418 cell comprising a nucleic acid containing a resistance gene to an antibiotic, in particular hygromycin B, and a nucleotide sequence coding for the non-structural proteins, and having the property of replicating the HCV at a concentration of antibiotic, in particular of hygromycin B, of 800 to 1000 μg/ml.

The invention also relates to a process for producing the hepatitis C virus, which comprises the infection of Vero/G418 cells, in particular of Vero/G418 cells as deposited at the CNCM on the 13 of Apr. 2001 under the number I-2659, by the hepatitis C virus and the culturing of these infected cells under suitable conditions.

The Vero/G418+ replicon cells are tested in a first step by infection from a titrated HCV viral stock in order to determine if this cell line can be infected and is capable of viral production.

Then, it is necessary to clone the sequences of the most functional replicons in order to place them back in the complete cDNA of the HCV, and to transfect the Vero/G418+ replicon or Vero/G418 cells in order to determine whether there is infectivity and viral production.

The most functional replicon is advantageously obtained from the cell which resists the greatest hygromycin B concentration. The growth of the cell indicates a greater expression of the hygromycin B resistance gene, which is linked to the replication efficacity of the replicon.

The infectivity determined here is the infectivity of the complementary DNA of the HCV, that is to say the possibility of reconstituting infectious viral particles after transfection of cells by RNA resulting from the transcription of the cDNA of the HCV. The virus is then capable of propagating itself on a suitable cell culture and of producing a quantity of viral particles.

The invention also relates to a process for replicating the hepatitis C virus by transformation of Vero/G418 cells with a nucleic acid as defined above, and in particular by transformation of the Vero/G418 cells as deposited on the 13 of Apr. 2001 at the CNCM under the number I-2659, in order to obtain transformed Vero/G418 cells, in particular those deposited on the 13 of Apr. 2001 at the CNCM under the number I-2658, and by culturing these transformed cells under suitable conditions.

The replication of the HCV can take place only in certain cells that it is useful to select. For this, a replicon is used, the minimum unit of replication, which contains the sequences of the hygromycin B resistance gene, inserted in place of the sequences coding for the structure proteins of the HCV. The possibility that certain cells have of growing in selective medium (for example DMEM/10% FCS and hygromycin B) is an indication of the replication of the genome of the HCV as the hygromycin B resistance gene is added by the HCV. The selection of resistant cells also means selection of genomes of the HCV that are capable of replicating themselves in these cells. As a consequence, the replication of the HCV is linked to the selection of the resistant cells.

This process therefore rests on a method of selection of cells that are capable of replicating the genome of the HCV.

The invention also relates to a process for producing the hepatitis C virus by transformation of Vero/G418 cells, in particular of Vero/G418 cells as deposited on the 13 of Apr. 2001 at the CNCM under the number I-2659, with a nucleic acid coding for the structural and non-structural proteins of the HCV, by the culturing under suitable conditions of the transformed Vero/G418 cells and the recovery of the HCV virus particles.

In a first step, cells growing under pressures of 1.5 to 2.0 mg/ml of hygromycin B are selected, then the total RNA of these cells is extracted in order to convert the RNA of the HCV to DNA. This is then cloned in a pGEM 3Zf vector (Promega) in which only the sequence coding for the non-structural proteins of the replicon is reintroduced in place and instead of the complete cDNA of the HCV. Thus, all the variations necessary for a better replication of the HCV on the cells used are introduced. The DNA obtained is then converted to RNA and this RNA serves for the transfection of the Vero/G418 cells in order to determine if a viral production is possible on these cells.

The invention also relates to a process for screening anti-HCV agents, which comprises the following steps:

- the introduction of the compound tested for its anti-HCV properties with transformed cells, constituted by Vero/G418 cells, comprising a nucleic acid chosen from:
  - those coding for the structural and non-structural proteins of the HCV or
  - those coding for the non-structural proteins of the HCV or
  - the replicons containing a resistance gene to an antibiotic, in particular hygromycin B, and a nucleotide sequence coding for the non-structural proteins of the HCV, and in particular with cells as deposited on the 13 of Apr. 2001 at the CNCM under the number I-2658,

- the extraction of the total RNAs of said cells, and
- the analysis of any reduction in the rate of synthesis of the RNA of the HCV of said cells relative to a control value corresponding to the rates of synthesis of the RNAs of the HCV of the cells in the absence of said tested compound.

The Vero/G418+ replicon cells growing at hygromycin B concentrations of 800 to 2000 μg/ml are subjected to the action of specific inhibitors of the 3-hydroxy-3-methylglutaryl coenzyme A reductase, such as mevastatin or lovastatin. Then, RNA extractions are carried out at variable moments on cells treated with these inhibitors. The synthesis of the RNAs of the HCV is then analysed by RT-PCR in a single step using a device called LightCycler (Roche) or by hybridization of the RNAs on filters using HCV-specific radioactive probes.

The following system can also be used which involves reproducing a replicon which also contains the sequences coding for the GFP protein the property of which is to fluoresce naturally under a certain wavelength. Moreover, this protein is chosen with a relatively short half-life. Under these conditions, it is not necessary to fix the cells and the fluorescence can be observed in real time. If an effective inhibitor of the HCV is placed in contact with the Vero/G418+ replicon cells and an inhibition of the synthesis of the RNA of the HCV is observed, this is also observed at the stage of the synthesis of the proteins produced, and as a result on the intensity of fluorescence produced by the GFP. As the half-life period of the GFP is then very short, a reduction is observed in the fluorescence of the GFP in the cells.

The invention relates to the use of hypocholesterolemiants, in particular statins, and more particularly lovastatin, mevastatin, simvastatin, pravastatin and fluvastatin, for the production of medicaments for the treatment of hepatitis C.

Statins are products used for the treatment of hypercholesterolaemia. They act at the level of the hydroxymethylglutaryl (HMG) CoA synthetase enzyme in order to block the synthesis of mevalonic acid. Mevalonic acid, which participates in the biosynthesis route of cholesterol, likewise produces geranyl or farnesyl by polymerization.

Thus, the statins, in blocking the synthesis of mevalonic acid, also affect the synthesis of the farnesyl or geranyl groups; they therefore have an indirect effect on prenylation.

These statins can therefore be used in order to verify the anti-HCV screening process as defined above.

Chemical Formulae of Some Statins:

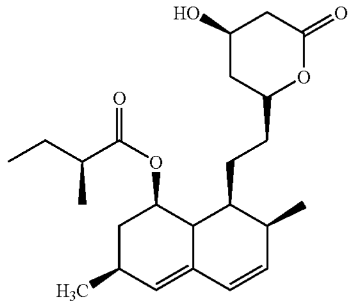

Lovastatin

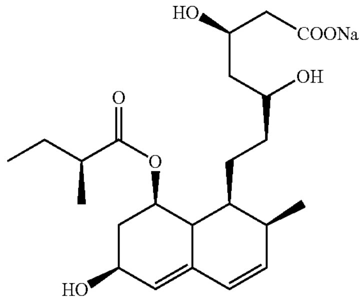

Pravastastin

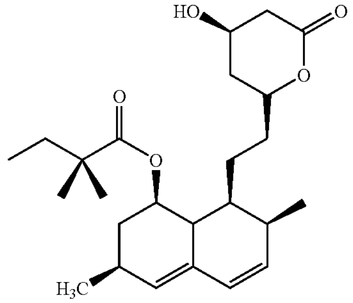

Simvastatin

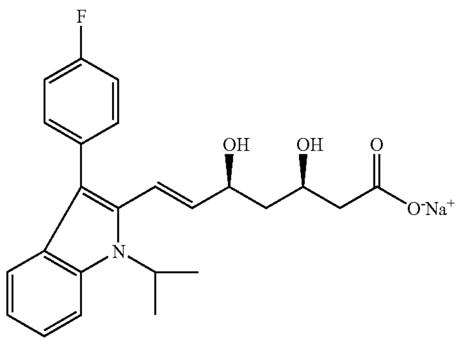

Fluvastatin

The invention also relates to the use of prenylation inhibitors, for the production of medicaments for the treatment of hepatitis C, where applicable in combination with an antiviral compound.

The invention relates to a process for preparing Vero/G418 cells comprising a nucleic acid chosen from:
- those coding for the structural and non-structural proteins of the HCV or
- those coding for the non-structural proteins of the HCV or
- the replicons containing a hygromycin B resistance gene and a nucleotide sequence coding for the non-structural proteins of the HCV, said process comprising the following steps:
- the insertion of one of the nucleotide sequences as defined above into the Vero/G418 cells,
- the subjection of the cells thus obtained to increasing concentrations of hygromycin B, in particular from 800 to 1000 µg/ml.

The invention relates to cells as obtained by implementing the process as defined above.

The invention relates to a pharmaceutical composition, characterized in that it comprises, as active ingredient, a prenylation-inhibiting compound, in combination with an antiviral agent and a pharmacologically acceptable excipient.

Prenylation is important for the NS5A protein as it promotes protein-protein interactions; all the perturbations of these interactions act on the process of replication of the HCV and reduce its efficacity.

The combination of a prenylation inhibitor which reduces the rate of replication of the HCV also involves a reduction of the viral load of the HCV in an infected patient. Because of this, the combined action with an antiviral agent must lead to a better elimination of the virus in the infected patients.

The invention relates to a pharmaceutical composition, characterized in that it comprises, as active ingredient, a hypocholesterolemiant compound, in combination with an antiviral agent and a pharmacologically acceptable excipient.

A compound acting on the synthesis of mevalonic acid has an action on the rate of prenylation of the NS5A protein of the HCV and consequently on the replication of the HCV. The combination with a hypocholesterolemiant compound, which acts indirectly on the replication of the HCV, also involves a reduction of the viral load of the HCV in an infected patient. Because of this, the combined action with an antiviral agent must lead to a better elimination of the virus in infected patients.

The hypercholesterolemiant compound used is chosen from lovastatin, mevastatin, simvastastin, pravastastin and fluvastastin.

The pharmaceutical compositions according to the invention are in particular in the form of 20 mg tablets, the daily dose being between 10 and 40 mg.

DESCRIPTION OF THE FIGURES

FIG. 2A corresponds to the indirect immunofluorescence obtained on Vero/G418+ replicon cells using a monoclonal mouse antibody directed against the capsid protein C.

FIG. 2B corresponds to the indirect immunofluorescence obtained on Vero/G418+ replicon cells using a serum of a patient infected by the HCV.

FIG. 2C corresponds to the indirect immunofluorescence obtained on Vero/G418+ replicon cells using a polyclonal antibody produced in the rabbit and directed against the NS4 protein.

FIG. 2D corresponds to the indirect immunofluorescence obtained on Vero/G418 cells (control cells) using a polyclonal antibody produced in the rabbit and directed against the NS4 protein.

FIG. 3A represents the result of the immunoprecipitations obtained using a rabbit polyclonal antibody directed against the NS5A protein, and carried out on cellular extracts originating in Vero/G418 (or Vn5) cells, infected either only by the recombinant vaccine virus vTF7-3 (line 1), or by the recombinant vaccine viruses vTF7-3 and vvNS5A (line 2), and labelled either in the presence of mevalonic acid $H^3$, or in the presence of methionine $S^{35}$. The immunoprecipitated NS5A protein is indicated by an arrow.

FIG. 3B represents the result of the immunoprecipitations obtained using a rabbit polyclonal antibody directed against the NS5A protein and carried out on cell extracts originating in Vn5 (Vero/G418) cells infected by the recombinant vaccine viruses vTF7-3 alone (line 1), vTF7-3 and vvNS5A.1a (line 2) and vTF7-3 and vvNS2-5B (line 3). The presence of the NS5A protein is indicated by an arrow.

FIG. 3C represents the result of the immunoprecipitations obtained using a rabbit polyclonal antibody directed against the NS5A protein and carried out on cell extracts originating in Vn5 (Vero/G418) cells infected by the recombinant vaccine viruses vTF7-3 alone (line 1), vTF7-3 and vvNS5A.1a dl1 (deletion of the amino acids situated between positions 1973 and 2100, line 2), vTF7-3 and vvNS5A.1a dl2 (deletion of the amino acids situated between positions 1973 and 2073, line 3), vTF7-3 and vvNS5A.1a dl3 (deletion of the amino acids situated between positions 1973 and 2001, line 4), and vTF7-3 and vvNS5A.1a (line 5), and labelled either in the presence of mevalonic acid $H^3$, or in the presence of methionine $S^{35}$. The position of the different truncated NS5A.1a proteins is indicated by a line on the side of the figure.

FIG. 3D represents the result of the immunoprecipitations obtained using a rabbit polyclonal antibody directed against the NS5A protein and carried out on cell extracts originating in Vn5 (Vero/G418) cells infected by the recombinant vaccine viruses vTF7-3 and vvNS5A of genotype 1a, vTF7-3 and vvNS5A of genotype 1b originating in two different patients (lines 1 and 2), and labelled in the presence of mevalonic acid $H^3$. The position of the NS5A protein is indicated by an arrow.

EXPERIMENTAL PART

I—Prenylation: Materials and Methods

Figure 1:
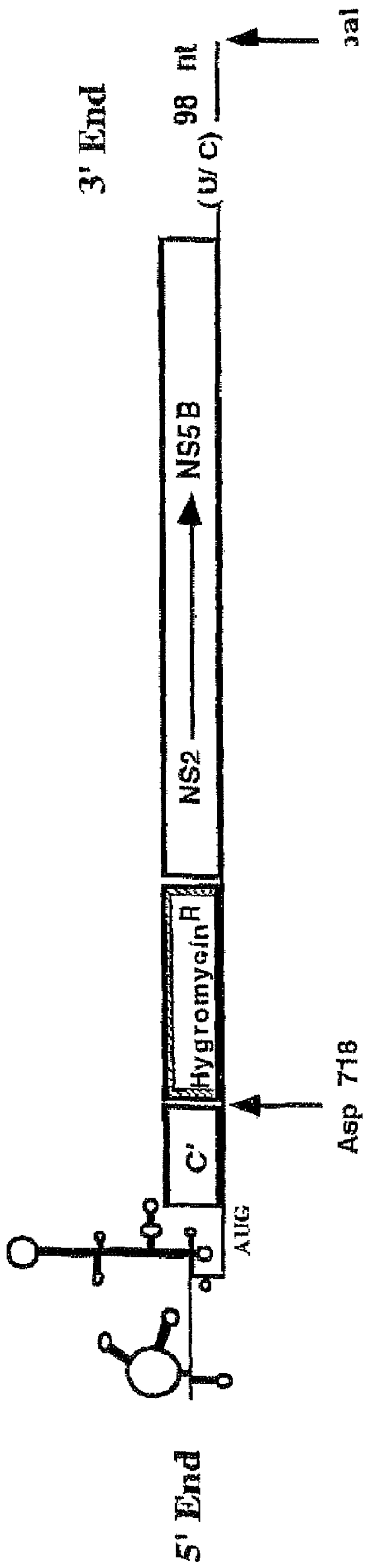
FIG. 1 is a diagram of the replicon of the 1a genotype of the hepatitis C virus. Said replicon contains: the 5' and 3' sequences corresponding to the non-coding regions of the HCV; the nucleotide sequence coding for a part of the capsid protein (C'), that is to say the 246 nucleotides (amino acids 1 to 82); the nucleotide sequence coding for the hygromycin B phosphotransferase gene, which is the selection gene (designated Hygromycin® on the diagram); the nucleotide sequences coding for the non-structural proteins corresponding to: NS2-NS3-NS4A-NS4B-NS5A-NS5B and designated NS2→NS5B. The Asp 718 site is one of the restriction sites included in the nucleotide sequence of the capsid protein which served for the insertion of the sequences coding for the selection gene. The XbaI restriction site is the site which is used to linearize the DNA before transcription. This site is then modified according to the method described in the "Materials and Methods" part.

1. Cells and Maintenance Conditions.

Vero/G418 cells: The Vero/G418 (or Vn5) cells (Frese et al., 1995) are cultured in thin layers in 10 mm dishes and in a DMEM medium (Dulbecco's Modified Eagle's Medium) and containing 10% foetal calf serum (FCS). The cells can be cultured under Neomycin pressure at 300 μg/ml (maintenance value for these cells). They are detached every 5 or 6 days by a trypsin/versene solution (NaCl 8 g/l; KCl 0.4 g/l; dextrose 1 g/l; $NaHCO_3$ 0.58 g/l; crystallized Trypsin 0.045 g/l; Versene 0.2 g/l) and $1\text{-}10^6$ cells are transferred into a 100 mm dish, which corresponds to a 1/10 dilution. The medium is changed every two to three days.

2. Cloning of the Genome of the Hepatitis C Virus.

Using primers specific to the sequence of the hepatitis C virus, a cDNA was synthesized according to the Gübler and Hoffman method (Gübler and Hoffman, 1983). Then, thanks to primers of known sequences, the genome of the hepatitis C was then able to be amplified by the so-called "nested primers" method (Mullis and Faloona, 1987). DNA fragments corresponding to different regions of the genome of the HCV as well as the sequences corresponding to the non-coding ends of the genome of the HCV virus were cloned in a pGEM 3Zf(+) vector (Promega) in the single restriction site Sma1. This vector contains the ampicillin resistance gene, the origin of replication of the plasmid and the intergenic fragment of the phage f1. Moreover, the fragments are placed under the control of the promoter T7 at the 5' end of the HCV or SP6 at the 3' end of the HCV. All these clones were constructed with overlapping DNA sequences in order to facilitate the in vitro recombinations. After total or partial digestions of the DNA of these different clones, fragments were purified on agarose gel and ligated together so as to reconstitute the genome of the hepatitis C virus. A 9623 nucleotide long cDNA was thus able to be generated.

3. Construction of the Recombinant pTM1 Plasmids and Production of the Corresponding Recombinant Vaccine Viruses.

Different DNA fragments coding for the proteins of the HCV and in particular for the NS5A protein of the HCV were generated by enzyme amplification from the genome of the HCV (pG/HCV 1-9623). These DNAs were inserted at the EcoRI restriction site in the multiple cloning region of the pTM1 plasmid (Moss et al., 1990). This region is situated immediately downstream from the promoter of the RNA polymerase of the phage T7 and of the IRES (internal ribosomes entry site) of the EMCV virus (*Encephalomyocarditis virus*).

The corresponding recombinant vaccine viruses were generated by homologous recombination according to the principle defined by Kieny et al. (1984). The recombinant viruses are purified by formation of colonies on 143 B tk-cells (cells deficient in thymidine kinase, ATCC CRL-8303) in the presence of bromodeoxyuridine (50 μg/ml). Each viral stock deriving from an isolated colony was amplified on CV1-L cells (strain resulting from the sub-cloning of kidney cells of African green monkeys) after infection with a multiplicity of infection (m.o.i.) of 1 colony-forming unit per cell (CFU/cell) (Fourmillier et al., 1996).

4. Analysis of the Proteins Expressed Using the Recombinant Vaccine-HCV Viruses.

($^{35}S$) labelling of the proteins: Vero/G418 (Vn5) cells were infected either with the vTF7.3 virus (Fuerst et al., 1986) alone, or co-infected by this virus and one of the recombinant viruses expressing the NS5A protein of the HCV, each with an m.o.i. of 5 CFU/cell. After an hour at 37° C., the inoculum is removed and replaced by DMEM medium containing 5% of foetal calf serum. At 16 hours post-infection, the cells are washed with DMEM medium without methionine, and incubated in this medium for 1 to 2 hours, then labelled for 3 hours with 100 μCi/ml of methionine ($^{35}S$) ($^{35}S$-Protein Labeling Mix (NEN), labelling solution). After this time, the medium is eliminated and the cells are then washed with PBS, and finally are lysed using a lysis buffer for cytoplasmic extraction (50 mM Tris-HCl pH 7.5; 150 mM NaCl; 1 mM EDTA; NP40 (or Igepal) 1% (Sigma); Na deoxycholate 0.1%; Aprotinin 10 μg/ml; TPCK (Sigma) and PMSF (Sigma), 20 μg/ml) or for total extraction by a lysis solution containing: 50 mM Tris-HCl pH 7.5; 150 mM NaCl; 1 mM EDTA; 0.5% NP40; 0.5% Na deoxycholate; 0.2% SDS; Aprotinin 10 μg/ml; TPCK and PMSF, 20 μg/ml. The proteins of the HCV are then immunoprecipitated from this lysate using polyclonal rabbit sera as described by Wychowski et al. (1985) and the precipitates were analysed by SDS-PAGE.

Mevalonic acid ($^3H$) labelling of the proteins: Vero/G418 (Vn5) cells were infected either with the vTF7.3 virus (Fuerst et al., 1986) alone, or co-infected by this virus and one of the recombinant viruses expressing the NS5A protein of the HCV, each at a m.o.i. of 5 CFU/cell. After an hour at 37° C., the inoculum is removed and replaced by DMEM medium containing 10% of foetal calf serum in the presence of Mevastatin (100 μg/ml). After 4 hours, 100 mCi/ml of mevalonic acid ($^3H$) are added to the medium. After 18 hours post-infection, the cells are washed with DMEM medium, the medium is eliminated and the cells are washed with a PBS solution before being lysed by a buffer containing: 50 mM Tris-HCl pH 7.5; 150 mM NaCl; 1 mM EDTA; 0.5% NP40; 0.5% Na deoxycholate; 0.2% SDS; Aprotinin 10 μg/ml; TPCK and PMSF, 20 μg/ml. The proteins of the HCV are then immunoprecipitated from this lysate using polyclonal rabbit sera as described previously and the precipitates are analysed by SDS-PAGE.

II—Analyses of the Replicon of the HCV: Materials and Methods

1. Construction of the Replicon of the HCV from the Complementary DNA of the HCV.

Starting from the clone containing the whole of the sequence of the HCV (pG/HCV 1-9623), a replicon of the HCV was initially constructed in which the sequences coding for the structural proteins were substituted by the sequences coding for Neomycin. The DNA corresponding to the neomycin gene was introduced between the Asp718 restriction sites (position 579 of the nucleotide sequence of the HCV of genotype 1a) and the Eco47III restriction site (position 2847 of the nucleotide sequence of the HCV of genotype 1a). A DNA fragment corresponding to the sequence coding for Neomycin was amplified using complementary primers of the sequence coding for Neomycin and containing at 5' and 3' extremities the Asp718 and Eco47III restriction sites. The amplified fragment was purified on a low melting gel (agarose gel with a low melting point), then this fragment was digested by the aforementioned restriction enzymes. This fragment was then integrated in the pG/HCV 1-9623 plasmid, deleted from its sequence between Asp718 and Eco47III. The sequences were thus inserted so as to be in phase with a remaining part of the sequences coding for the capsid protein and with the sequences coding for the NS2 protein. However, because of the position of the Eco47III restriction site, the terminal NH2 part of NS2 was deleted. As a result, the whole of the NS2 sequences was reconstituted by amplifying with PCR the whole of the sequences coding for NS2 and part of the sequence coding for the NS3 protein. The primer in 5' position of the sequence also contains the sequences of the SpeI restriction site. The DNA fragment was amplified and purified according to the customary procedures, then it was digested by the SpeI enzymes and the Bst1107I enzyme, the site position of which is in position 3640 of the nucleotide sequence of the HCV of genotype 1a. Finally, this fragment was integrated between the SpeI and Bst1107 I restriction sites. The resulting pG/Neo 2-5B plasmid was obtained. This plasmid contains the non-coding 5' and 3' regions, part of the sequence coding for the capsid protein C, the sequences of the neomycin resistance gene and the whole of the sequences coding for the region of the non-structural proteins of the HCV. It appears in this construction that the capsid part is fused with the neomycin resistance gene and with the NS2 product of the HCV. The other proteins of the HCV will normally be produced by cleavages which will be generated by the two viral proteases of the HCV. As the Vero/G418 cells are resistant to neomycin, the pG/Neo 2-5B plasmid was used to substitute the sequences coding for neomycin with the sequences coding for the hygromycin B resistance gene. A DNA fragment containing the hygromycin B resistance sequences as well as the sequences of the Asp718 and XbaI restriction sites located respectively at the 5' and 3' ends was amplified. The XbaI site is compatible with the SpeI site, but after hybridization, the SpeI and XbaI sites will not be generated. The unique SpeI site disappears from the sequence. This DNA fragment has thus been integrated between the Asp718 and SpeI sites of the pG/Neo 2-5B plasmid. After transformation and selection, a pG/Hygro 2-5B plasmid was obtained in which the sequences coding for the neomycin resistance gene were replaced by those coding for the hygromycin B resistance gene, the other sequences being exactly preserved.

2. Transcription of the complementary DNA of the HCV to RNA

Transcription for transfection: For large scale production of RNA the Promega kit (Ribo MAX™ Large Scale RNA production system-T7) was used. The DNA corresponding to the replicon was linearized beforehand and its ends blunted. At the 3' end of the genome of the HCV, a restriction site was placed in order that after digestion by the restriction enzyme XbaI and treatment with mung bean nuclease (Biolabs)(Kowalski et al., 1976), the surplus bases are digested, which corresponds henceforth to the authentic end of the RNA of the HCV. The treatment is carried out on 5 μg of DNA. After phenol and chloroform extraction of the DNA preparation, the DNA is recovered by precipitation with ethanol. Once centrifuged, the DNA is taken up in sterile water which has been treated with DEPC (Diethylpyrocarbonate), in order to avoid any trace of Rnase. The DNA can then be transcribed to RNA. Thus, in a sterile Eppendorf tube, 20 μl of DNA (approximately 5 μg) are supplemented by: 20 μl of water treated with DEPC, 20 μl of 5× transcription buffer (Hepes-KOH (pH 7.5) 400 nM, $MgCl_2$ 120 mM, spermidine 10 mM, DTT 200 mM), 30 μl of rNTPs (25 mM ATP, CTP, GTP, UTP), 10 μl Enzyme Mix (T7) (Promega) and the mixture is incubated at 37° C. for 2 to 4 hours. Once the DNA has been transcribed by the T7 RNA polymerase, the DNA matrix is degraded by 5 μl of RQ1 Dnase (Rnase free) (Promega) for 15 to 30 minutes at 37° C. A phenol/chloroform extraction is carried out and the aqueous solution containing the RNA is precipitated by adding 1/10 of 3M sodium acetate and two volumes of ethanol. After one night, it is centrifuged in order to recover the RNA pellet. The latter is then washed with a 70% ethanol solution, then dried lightly on the bench then finally resolubilized with sterile water treated with DEPC. The RNA is subsequently stored at −80° C.

Transcription for radioactive labelling: A Promega transcription kit is used. The DNA used as a matrix for the production of radioactive RNA originates from DNA amplified by the PCR method and in which the primers in 5' or 3' position contain the sequences of the promoters for the bacteriophages T7 or SP6 which thus allows production of RNAs of negative or positive polarity according to whether it will be sought to characterize respectively the RNAs of positive or negative polarity of replicons. It is not necessary to linearize the DNAs produced by PCR with a restriction enzyme since the ends are blunt. However, the DNA fragments will be purified on low melting gel (agarose gel with a low melting point) before being transcribed. 3 μl of DNA (corresponding to 1-2 μg) are supplemented by 4 μl of 5× transcription buffer (Tris-HCl (pH 7.9 at 25° C.) 200 mM, NaCl 50 mM, $MgCl_2$ 30 mM, spermidine 10 mM), 2 μl of a solution of DTT 100 mM, 0.5 μl of RNasin (inhibitor) (40 U/μl) (Blackburn and Moore, 1982), 4 μl of a mixture of rNTPs (rATP, rUTP and rGTP, each 2.5 mM) from which the rCTP has been omitted, 5.5 μl of water treated with DEPC, 1 μl of T7 polymerase enzyme (20 U/μl) and 50 μCi of lyophilized dCTP $\alpha P^{32}$. The DNA is transcribed for 1 hour at 37° C. Then the DNA is degraded as previously described and the RNA is precipitated and resolubilized in water treated with DEPC.

3. Electroporation Technique

This technique was carried out according to a procedure described by Liljeström et al. (1991). The apparatus used for the electroporations is a BioRad product (BioRad Gene Pulsar with Pulse Controller). The Vero/G418 cells were seeded on 100 mm dishes, in a DMEM medium supplemented by 10% of foetal calf serum (FCS) and they were left in culture until a confluence of 80 to 90% was achieved. It is to be noted that $5\times10^6$ cells are necessary for each electroporation. As a consequence, the number of dishes is calculated in order to have a sufficient quantity of cells available. The cells to be electroporated are washed with a solution of PBS and are then detached with the help a trypsin solution containing EDTA. This solution is discarded, and after a few minutes the cells which detach are taken up in DMEM/10% FCS medium and centrifuged at 800 rpm for 6 minutes. The cells are then suspended and rewashed in a PBS solution, after centrifugation, the cell pellet is then taken up in a volume of PBS medium so that the final cell concentration is $1\times10^7$ cells/ml. These are stored in ice. In a 0.2 mm electroporation cuvette of the BioRad make, 500 μl of the $1\times10^7$ cells/ml cell suspension are placed in contact with 30 μg of RNA (RNA of the replicon) and the same tube is placed in the electroporation apparatus which has been calibrated to 1.75 kV and 25 μFD, while the resistance controller was on the infinite position (∞ button of the apparatus). The cells thus received two electric shocks. The percentage of cells which survive these shocks is 20 to 30%. After these shocks, the cells are taken up in DMEM 10% FCS medium and are kept at room temperature for 10 minutes before being re-seeded on a 100 mm dish. Then all the dishes are placed in a $CO_2$ oven and at a temperature of 37° C. They are then ready to be subjected to the hygromycin B selection pressure.

4. Selection of the Hygromycin B Resistant Cells.

The Vero/G418 cells electroporated in the presence of the RNA of the HCV and containing the hygromycin B resistance gene were used for a progressive pressure in the presence of hygromycin B. Once electroporated, as described previously, the cells are initially deposited on 100 mm dishes. After 48 hours, the cells are subjected to a low hygromycin B pressure of 100 μg/ml, then to 200 μg/ml until they reach confluence. They are then detached by the action of the trypsin/versene mixture and they are transferred into 60 mm dishes, while keeping the initial selection pressure. The cells are kept for five to ten passages (variable) at this concentration in order to stabilize the cell population. Subculturing takes place at first approximately every three weeks with a ½ dilution of the cells and a change of medium every three to four days. After a stabilization of cell growth (subculturing on average every 10 to 15 days, observations likewise regarding the general state of the cell), these are subjected to increasing hygromycin B pressures of the order of 50 to 100 μg/ml according to the circumstances. The stabilization of the cell often takes place after five passages under the defined pressure. The total RNA of the cells growing under selective pressure was extracted and subjected to a RT-PCR (PCR using retrotranscriptase) in the non-coding 5' and 3' regions. As these proved to be positive, the selection pressure was maintained and progressively increased. However, studies using indirect immunofluorescence did not allow the proteins of the HCV to be detected. Detection by immunofluorescence was possible only for cells growing under hygromycin B pressures greater than 600 μg/ml. The cells were also frozen at intermediate selection pressures. Cells growing under a hygromycin B pressure of 1000 μg/ml are currently available.

5. Cells and Maintenance Conditions.

Vero/G418/HCV replicon cells: The cells are cultured in a thin layer in 75 $cm^2$ bottles and in a DMEM medium containing 10% of foetal calf serum (FCS) and hygromycin B. The hygromycin B concentration depends on the selection of the cell. The latter varies from 200 to 1000 μg/ml. The 75 $cm^2$ bottles are customarily seeded with $5\times10^6$ cells, which corresponds to a dilution by half and they are kept for 10 to 15 days according to their density. At the time of their passage, the medium of these cells is discarded and the cells are washed twice with a trypsin/versene medium (NaCl 8 g/l, KCl 0.4 g/l, dextrose 1 g/l, $NaHCO_3$ 0.58 g/l, crystallized Trypsin 0.045 g/l, Versene 0.2 g/l). The cells very quickly detach after a few minutes (2 to 5 minutes). These cells are then taken up in DMEM medium containing the suitable hygromycin B concentration and the cells are distributed in two bottles. The cells are left to fix and establish themselves on the bottle and the medium is not changed until three to four days afterwards, then every other day until the desired cell density (8 to $10\times10^6$ cells/75 $cm^2$ bottle) is achieved.

6. Analysis of the Proteins by Indirect Immunofluorescence

Figure 2:
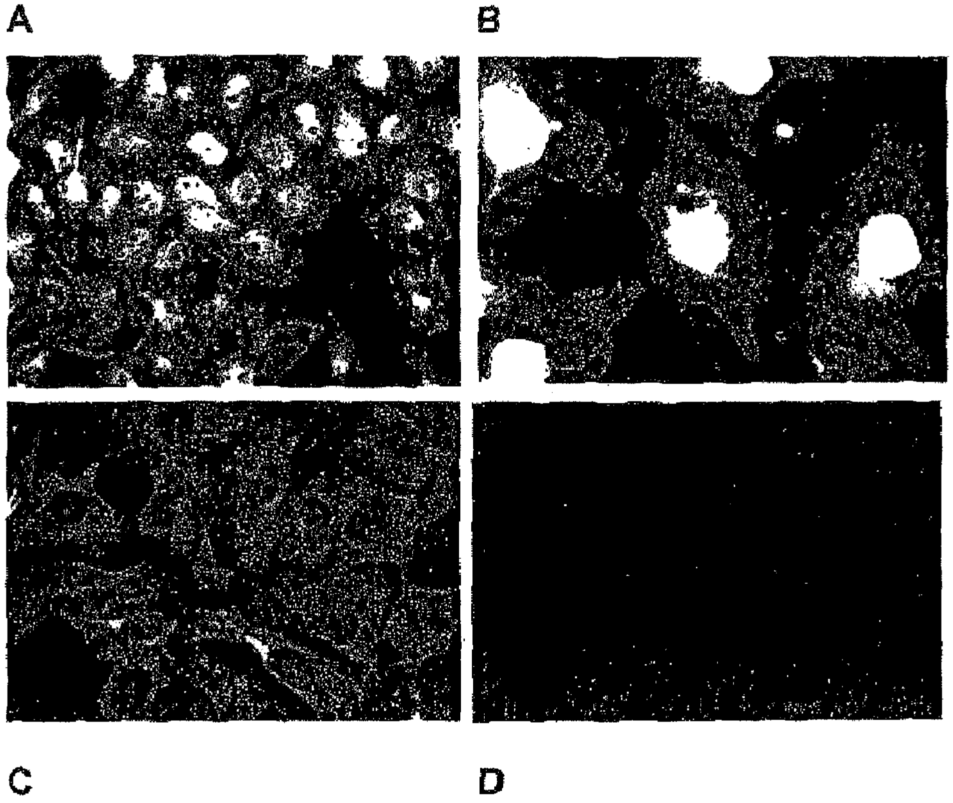
FIGS. 2A to 2D represent immunofluorescence results on the Vero/G418+ replicon cells. The Vero/G418 cells are cultured on glass sheets in the absence of hygromycin B (FIG. 2D) and the Vero/G418+ replicon cells in the presence of hygromycin B (800 µg/ml) (FIGS. 2A, 2B and 2C). These cells are then treated according to the methods described in the "Materials and Methods" part.

The Vero/G418 cells are cultured on glass sheets in the absence of hygromycin B and the Vero/G418+replicon cells in the presence of hygromycin B (800 μg/ml). After 3 days of culture the cells are fixed in a PBS solution containing 4% of paraformaldehyde. The cells fixed with the paraformaldehyde are then treated with a Triton X-100 solution in order to encourage intracellular labelling. The cells are then placed in contact with specific antibodies directed against different proteins of the HCV and diluted in TBS (Tris-buffered saline: 20 mM Tris-HCl pH 7.5; 137 mM NaCl; 2 mM EDTA). These antibodies are either monoclonal antibodies directed against the capsid, NS3 or NS5 protein and prepared in mice, or polyclonal antibodies recognizing the NS4 or NS5A or B protein and prepared in rabbits, or anti-HCV antibodies originating in patients infected by the HCV. After several rinses, the cells are then incubated with a secondary rhodamine-coupled antibody (anti-mouse immunoglobulins produced in rabbits; DAKO) or fluorescein-coupled antibody (anti-mouse immunoglobulins produced in donkeys; Jackson), or secondary rhodamine- or fluorescein-coupled antibodies and recognizing rabbit immunoglobulins or human immunoglobulins. The thus-labelled cells are then observed with a fluorescence microscope (Zeiss) and photographed (see FIG. 2).

7. Purification of the RNAs.

a) According to the Method Described in the Promega Kit (SV "Total RNA Isolation System" Kit).

RNA purifications can be carried out on $1.5\times10^3$ to $5\times10^6$ cells. The extraction procedures are carried out with the Promega kit (SV Total RNA Isolation System) and described according to the Promega manual. For adherent cells, the medium is removed and the cells are washed twice with a trypsin/versene solution, once the cells have been detached. These are then taken up in the culture medium and are centrifuged at 300 g for 5 minutes. The medium is then aspirated and the cells are taken up in a PBS solution and recentrifuged as described previously. The medium is aspirated and the cell pellet can be either treated for the rest of the operations or stored at −80° C. The rest of the protocol corresponds to the description of the Promega procedure: the cell pellet of cells is suspended in 175 μl of the lysis solution (SV RNA Lysis Buffer, supplied with the kit: 4M GTC (guanidine isothiocyanate); 10 mM Tris-HCl pH 7.5; 0.97% β-mercaptoethanol). The pellet is then dispersed by pipetting several times. If the cell concentration is between $1\times10^6$ and $5\times10^6$ cells, it is necessary to break the DNA by passing it through a very fine needle. 350 μl of a SV RNA Dilution Buffer (Promega) are then added to the 175 μl of the lysis solution. This is mixed by inverting the tube three to four times and the tube is then placed in a water bath raised to 70° C. and left to incubate for 3 minutes (this time must not be exceeded, in order not to risk degrading the RNA). This is centrifuged at 12000-14000 g for 10 minutes at 20-25° C. and the tubes which are provided with the kit are used for the remainder of the operation. Moreover, it is necessary to identify each tube for each preparation used and to wear gloves in order to avoid Rnases contaminations. The lysis solution is transferred into another centrifugation tube and the pellet must be prevented from becoming suspended again. 200 μl of ethanol at 95° C. are added to the aqueous solution. This is mixed by pipetting three to four times, then this solution is transferred onto a micro-column contained in the centrifugation tube and centrifuged at 12000-14000 g for a minute. The micro-column is removed from the tube, the liquid present in the collection tube is eliminated and the micro-column is then replaced on the original tube. 600 μl of the RNAs wash solution is added on the micro-column (RNAs wash solution: 60 mM potassium acetate, 10 mM Tris-HCl pH7.5 and 60% ethanol). This is centrifuged at 12 000-14 000 g for a minute. The collection tube is emptied again and replaced as previously. For each preparation to be purified, the following solution is prepared (and in this order): 40 μl Yellow Buffer (22.5 mM Tris-HCl pH 7.5; 1.125 M NaCl; 0.0025% Yellow dye (Promega) (w/v), 5 μl 0.09M $MnCl_2$ and 5 μl DNase I enzyme. The mixture must not be vortexed but must be mixed slowly. The whole is kept in ice and if the enzyme has to be defrosted, it must be left in the ice. The 50 μl of this solution are added on the membrane of the Spin Basket. It is necessary to ensure that the solution covers all of the membrane. This is left to act for 15 minutes at 20-25° C. (bench temperature). After this incubation period, 200 μl of a solution stopping the enzyme activity are added (SV DNase stop solution) (2M guanidine isothiocyanate, 4 mM Tris-HCl pH 7.5 and 57% ethanol). The micro-column is centrifuged at 12 000-14 000 g for a minute. 600 μl of a RNA wash solution (SV RNA wash solution) are added and this is centrifuged at 12000-14000 g for a minute. 250 μl of the RNA wash solution are added. This is centrifuged at maximum speed for two minutes. An elution tube of the initial kit is removed for each preparation and the micro-column is transferred into another centrifugation tube. 100 μl of water treated with DEPC are added on the membrane of the micro-column. This is centrifuged at 12000-14000 g for a minute. The RNA solution is contained in the elution tube and is stored at −80° C.

b) For Larger Quantities of RNA, the Promega Kit is used (Total RNA Isolation System).

The values given here are to be used for $1\times10^7$ cells. The preparation of the cells takes place in the same way as described previously. The principle of extraction of the RNAs is based on the method described by Chomczynski and Sacchi (1987) and which uses guanidium thiocyanate. The pellet of cells is suspended in 1.2 ml of a denaturation solution containing: 26 mM of sodium citrate (pH 6.8), 0.5% N-lauryl sarcosine, 0.125 M β-mercaptoethanol and 4M guanidine thiocyanate. The solution is separated into two Eppendorf tubes thus containing 600 μl of the solution. 60 μl of 2M sodium acetate are then added to each tube and the whole is mixed slowly, by turning over the tubes (4 to 5 times). This solution is then extracted with 600 μl of phenol: chloroform: IAA (isoamyl alcohol) and the tubes are then placed in ice for 15 minutes. After this time, the aqueous solution is recovered by centrifuging the tubes for 30 minutes at 14000 rpm at 4° C. in an Eppendorf machine. There must then be added to the aqueous solution an equivalent volume of isopropanol and after having mixed, the whole is left at −20° C. for 15 minutes. This is centrifuged at 14000 rpm at 4° C. for 30 minutes in order to recover the DNA residue which will be washed by a 75% ethanol solution. This is centrifuged anew, then the ethanol is discarded, and the pellet is then left to dry slightly, which will be suspended in 50 μl of Rnase free water (treated with DEPC). The purified RNA solutions can be collected together. The RNAs are then stored at −80° C.

c) Purification of the RNAs by Cesium Trifluoroacetate: CsTFA™ (Pharmacia Product)

Total RNA extracts prepared from cells or in certain cases starting from biopsies by the standard method using guanidium thiocyanate are also purified by centrifugation on cesium trifluoroacetate (CsTFA) according to the procedure described by Zarlenga and Gamble (1987). This thus allows a RNA preparation to be obtained that is devoid of DNA, of proteins and in certain cases of glycogen, for RNAs isolated from hepatocytes. The RNA previously isolated by guanidium thiocyanate is then purified on CsTFA (Pharmacia). The RNA is suspended in a solution of CsTFA with a density of 2.0 g/ml in order to finally be at a concentration of 1.65 g/ml and containing BET (ethidium bromide) at a concentration of 0.5 μg/ml. The solution contained in 5 ml polyallomer tubes (Beckman) is then centrifuged in a SW 55 Ti rotor (Beckman) for 44 hours at 15° C. and at 200000 g. After this centrifugation time, the RNA is removed and precipitated from a 0.3 M sodium acetate solution and from 2 volumes of ethanol at −20° C. during the night. This is then centrifuged in order to recover the RNA pellet, this pellet is washed in 70% ethanol, and the pellet is dried and the RNA is taken up in DEPC treated water. Other purifications are no longer necessary. The thus-prepared RNA can be used for amplification operations or for hybridization operations on filters.

8. Hybridization of the Total RNA of Cells Containing the Replicon by Radioactive Probes.

Preparation of the Filters: the Denaturation of the RNA Takes Place by a Glyoxal solution, then, after denaturation, the RNAs are fixed on nitrocellulose filters by aspiration (apparatus used, BioDot SF from BioRad). The purified RNAs, as previously described, are treated as follows: 22 μl of RNA are mixed with 9 μl of a 100 mM sodium phosphate solution (pH 7.0), 45 μl of DMSO (dimethyl sulfoxide (Sigma)) and 13.2 μl of a 6M glyoxal solution (Sigma). The whole is mixed and centrifuged in order to collect all of the liquid. The mixture formed by the RNA and the denaturing solution is thus incubated for an hour at 50° C., then the sample is cooled in ice. Two volumes of a 20×SSC solution (3 M NaCl; 0.3 M sodium citrate pH 7.0) are then added to each sample before their passage on the nitrocellulose membrane which will have been treated beforehand in a 10×SSC solution (1.5 M NaCl; 0.15 M sodium citrate pH 7.0). To eliminate the remaining glyoxal, the filter is passed into a solution heated to 95° C.: 20 mM Tris-HCl, pH 8.0; 1 mM EDTA and which is left under gentle stirring at room temperature. Each filter is then placed in an oven under vacuum (at 80° C.) for one to two hours.

Prehybridization and hybridization of the filters: The filter is placed inside a plastic bag and the prehybridization solution (10 mM EDTA; 7% SDS; 0.5 M $Na_2HPO_4$, pH 7.2) is added. The plastic bag is sealed and the whole is left in pre-hybridization for 5 minutes at 65° C. A corner of the plastic bag is then cut off and the pre-hybridization solution is removed. The same solution is then added to the bag with the radioactive probe at $10^6$ cpm/ml. The contents are thus left in hybridization for 4 to 24 hours at 65° C.

Washing of the filters: Different washes are carried out: first of all two washes for 5 to 10 minutes with a mixture containing a 2×SSC solution (0.3 M NaCl; 0.03 M sodium citrate pH 7.0) and 0.1% SDS. Two washes are then carried out at 50° C. for 15 minutes each with a mixture containing a 0.1×SSC solution ($1.5\times10^{-2}$ M NaCl; $1.5\times10^{-3}$ M sodium citrate pH 7.0), 0.1% SDS.

III—Process for Producing the HCV by Infection:

This process allows testing of whether the cells containing the replicon can produce HCV particles by infection.

At present there is no cell system capable of producing the hepatitis C virus. The introduction of cells capable of replicating the genome of the HCV involves the selection of factors which also encourage the multiplication of the virus. Once such cells have permitted a viral amplification, the purification of the virus can be envisaged as well as the inactivation of the latter for vaccination tests.

In order to infect cells from stocks of virus of strain H (Feinstone et al., 1981) (this is the same strain as was used to clone the complete cDNA of the HCV), or from a virus originating in infected patients, cells of the Vero/G418 type (or Vn5), the Vero/G418+ replicon cells under hygromycin B pressure type or the Vero/G418+ replicon cells without hygromycin B pressure type are used. These cells are kept in a normal medium (DMEM/10% FCS) and without hygromycin B in order to attenuate the action of the replicon. A RT-PCR is carried out on the initial virus, which allows quantification of the viral material (presence of RNA) without determining its infectious character at the same time. The cells are then infected by the viruses as mentioned above. The cells are kept and studied at different times in order to determine if there is amplification of the genetic material of the HCV. For this, samplings of cells are carried out and the total RNA of these cells is extracted in order to quantify the RNA of the HCV either by RT-PCR, or by hybridization of the RNAs on filters. Moreover, the aim is to learn if the virus is capable of lysing the cells or if it persists in the cell. If there is cell lysis, it is sufficient to take up the cell lysates in order to infect other cells. The quantification of the virus can then take place by various methods used in virology. Moreover, if the viral infection does not lead to a lysis of the cells, the multiplication of the HCV can be observed by indirect immunofluorescence using antibodies directed against proteins of the HCV.

IV—Infectivity Test for the Complete cDNA of the HCV Reconstituted with the Sequences of the Replicon by Transfection of Cells:

It is essential to reclone the sequences of the most functional replicons, i.e. those which showed the most effective replication by allowing the cell to resist very high concentrations of hygromycin B. Thus, the RNAs of these cells are extracted according to the procedures described above. The RNA of the replicons is amplified by RT-PCR in a single step, in order that the whole of the variations corresponds to the same replicon molecule. The DNA is sequenced and the RNA resulting from the transcription of the DNA is transfected anew in order to verify its replicative power on the cells. In the thus-obtained DNA sequence, the sequences corresponding to the hygromycin B resistance gene are substituted by the sequences coding for the structure proteins of the HCV. These sequences are cloned in a vector in order to be capable of producing RNA by transcription from DNA. These cDNAs serve to produce RNA in order to transfect by electroporation (see above) the Vero/G418 (or Vn5) cells, the Vero/G418+ replicon cells under hygromycin B pressure or the Vero/G418+ replicon cells without hygromycin B pressure. The identification tests are then carried out as described above.

V—Process for Screening Anti-HCV Agents:

As the cell growth under high hygromycin B pressures is dependant on the efficacity of replication of the replicon of the HCV, different anti-viral agents of the HCV were tested which can inhibit either directly or indirectly the replication of the HCV.

The Vero/G418+ replicon cells and the Vero/G418 (or Vn5) control cells are subjected in parallel to the action of different anti-virals and at variable concentrations. Any action on the replication of the replicon necessarily has a repercussion on the synthesis of the RNAs of the HCV and as a result on the synthesis of the proteins. Thus, the total RNAs of the cells subjected to the action of the anti-virals are extracted, then fixed on filters and finally hybridized with probes specific to the HCV. Moreover, as the synthesis of the proteins is affected by the reduction in the replication, a labelling of the proteins is carried out and the expression of the different proteins is studied by immunoprecipitation using antibodies directed against proteins specific to the HCV.

A replicon can also be used which contains in its sequence the sequences coding for the GFP. For this, a GFP with a short half-life is chosen (Clontech). The regeneration of this protein depends on the rate of synthesis but also on the replication of the replicon. Inhibitors acting on the replication of the HCV affect the synthesis of the proteins and consequently that of the GFP protein. The advantage of this approach is that it is not necessary to fix the cells in order to detect the GFP by immunofluorescence as it has the property of fluorescing naturally under certain wavelengths. The cells containing the replicon and the GFP and subjected to the action of anti-viral agents can be observed at different moments. Photos can be taken and the immunofluorescence of the GFP can then be analysed. Any reduction in or disappearance of the immunofluorescence of the GFP is evidence of the action of anti-virals of the HCV.

VI—Study of the Prenylation of the NS5A Protein of the HCV of Genotype 1a and 1b:

For this study, different recombinant vaccine viruses were used. They express the whole of the NS5A protein of the HCV of genotype 1a or of genotype 1b. For this latter genotype, the sequences coding for the NS5A protein were amplified from two patients infected by the HCV of genotype 1b. Certain constructions of the NS5A protein of the HCV contain deletions of the protein sequence located in the amino-terminal part of the protein. These different recombinant viruses correspond to: vvNS5A.1a dl1 (del 1973-2100 aa), vvNS5A.1a dl2 (del 1973-2073 aa) and vvNS5A.1a dl3 (del 1973-2001 aa). The amino acids which are deleted in the NS5A protein are given in brackets. For greater precision, the figure which corresponds to the position of the amino acid in the polyprotein of the HCV has been kept. Thus, del 1973-2100 aa corresponds to a deletion of the peptide sequence between the amino acids 1973 and 2100 of the polyprotein of the HCV. This deletion of the protein concerns the amino-terminal part of the NS5A protein. Moreover, a recombinant vaccine virus, vvNS2-5B, which expresses the NS2 proteins up to the NS5B protein of the HCV, that is to say NS2, NS3, NS4A, NS4B, NS5A and NS5B, has also been used.

Figure 3:
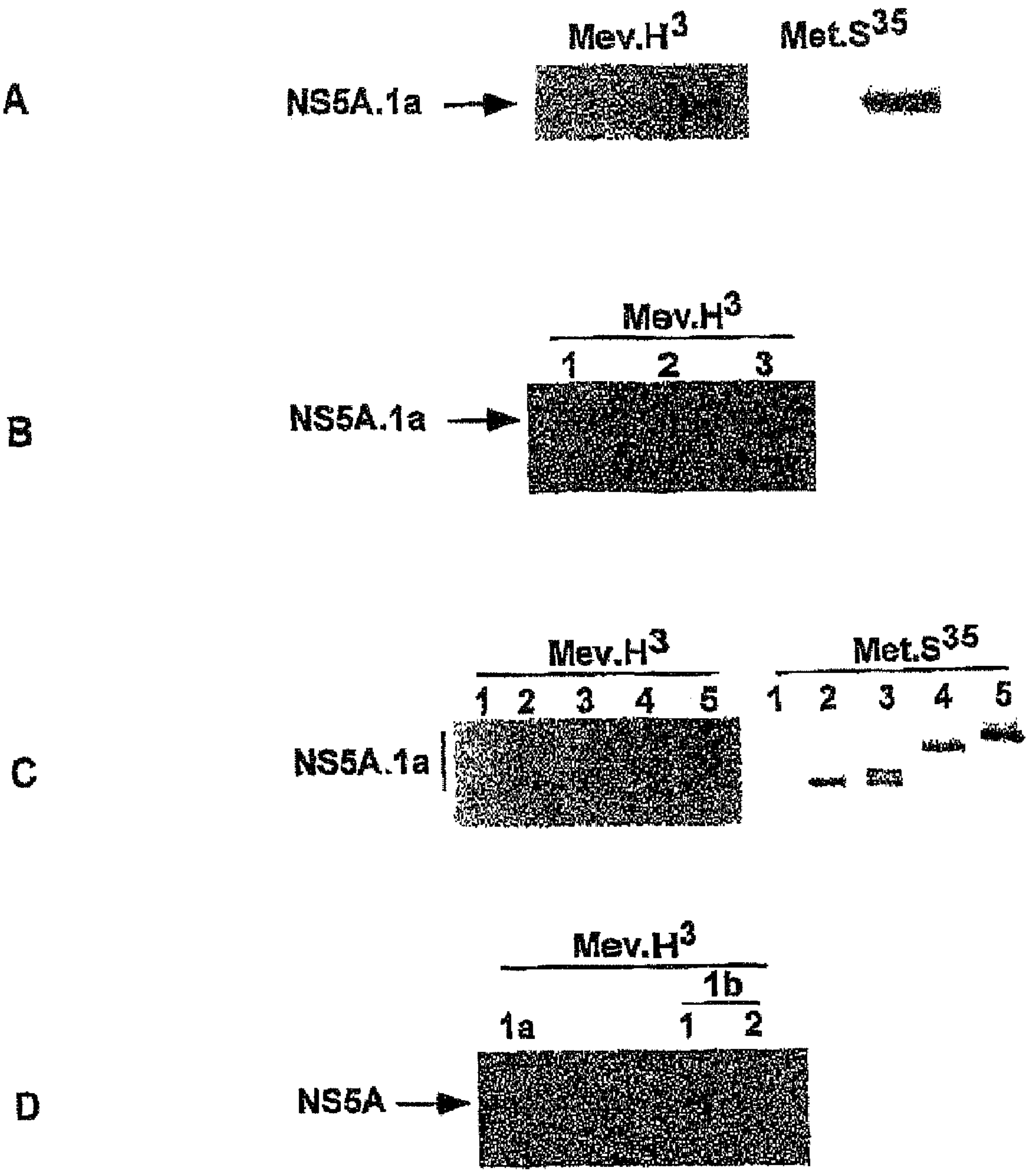
FIGS. 3A, 3B, 3C and 3D relate to the characterization of the prenylation of the NS5A protein of the hepatitis C virus.

The thus-infected cells are used to carry out metabolic labellings either in the presence of mevalonic acid ($H^3$) or in the presence of methionine $S^{35}$. The procedures used for these labellings are detailed below.

a) Mevalonic Acid ($H^3$) Labelling of the Proteins:

Vero/G418 (Vn5) cells were seeded on 6-well plates (Costar) at $10^6$ cells/well and in a DMEM medium (Dubelcco's modified Eagle's Medium) containing 10% of foetal calf serum (FCS). These cells are placed in a $CO_2$ oven and at 37° C. for 24 hours. They are then infected either with the vTF7.3 virus alone (Fuerst et al., 1986), or co-infected by this virus and one of the recombinant viruses expressing the NS5A protein of the HCV previously described, each at a m.o.i. of 5 CFU/cell. After an hour at 37° C., the inoculum is removed and replaced by DMEM medium (Dulbecco's modified Eagle's Medium) containing 10% of foetal calf serum and 100 μg/ml of mevastatin for a 4-hour pretreatment following which 100 μCi/ml of mevalonic acid ($H^3$) is added to the medium. After 18 hours post-infection, the cells are washed with DMEM medium, the medium is discarded and the cells are washed with a PBS solution before being lysed by a buffer containing: 50 mM Tris-HCl pH 7.5; 150 mM NaCl; 1 mM EDTA; 0.5% NP40; 0.5% Na deoxycholate; 0.2% SDS; Aprotinin 10 μg/ml; TPCK and PMSF, 20 μg/ml. The NS5A protein of the HCV is then immunoprecipitated from this lysate using a polyclonal rabbit serum directed against the NS5A protein according to a procedure already described (Wychowski et al., 1985) and the precipitate is analysed by SDS-PAGE. The result of these labellings is given in FIGS. 3A, 3B, 3C and 3D. The mevalonic acid labellings are indicated by: Mev.$H^3$. In FIGS. 3A, 3B and 3C, the lines 1 indicate the result obtained on a lysate originating in cells infected by the recombinant virus vTF7.3. In this case it is a control measure.

b) ($S^{35}$) Labelling of the Proteins:

Vero/G418 (Vn5) cells were infected with the same recombinant viruses as those mentioned previously. After an hour of placing in contact at 37° C., the inoculum is removed and replaced by DMEM medium containing 5% of foetal calf serum. At 16 hours post-infection, the cells are washed with DMEM medium without methionine, incubated in this medium for 1 to 2 hours, and labelled for 3 hours with 100 μCi/ml of methionine ($^{35}S$) ($^{35}S$-Protein Labeling Mix (NEN), labelling solution). After this time, the medium is eliminated and the cells are then washed with PBS, and finally are lysed using a lysis buffer containing: 50 mM Tris-HCl pH 7.5; 150 mM NaCl; 1 mM EDTA; 0.5% NP40; 0.5% Na deoxycholate; 0.2% SDS; Aprotinin 10 μg/ml; TPCK and PMSF, 20 μg/ml. The NS5A protein of the HCV is then immunoprecipitated from lysates using a polyclonal rabbit serum as described by Wychowski et al. (1985) and the precipitate is analysed by SDS-PAGE. The methionine $S^{35}$ labellings are indicated in FIGS. 3A and 3C by: Met.$S^{35}$. In FIGS.

3A and 3C, the lines 1 indicate the result obtained on a lysate originating in cells infected by the recombinant virus vTF7.3 and labelled with methionine $S^{35}$. In this case it is a control measure.

It will be noted that the NS5A protein of the HCV of genotype 1a or 1b is prenylated in the Vero/G418 (Vn5) cells (see FIGS. 3A and 3D). This prenylation takes place when the NS5A protein is expressed alone or in the context of the polyprotein (see FIG. 3B, lines 2 and 3 respectively). Prenylation is a post-translational modification process affecting principally the NS5A protein of the HCV of genotype 1a or 1b, and can affect the other genotypes.

REFERENCES

Blackburn P. and Moore S. (1982) The Enzymes, Vol. XV, Part. B, Academic Press, BY,
Bouffard et al. (1992) *The J. Infect. Diseases,* 166, 1276-1280,
Casey P. J. (1992) *Journal of Lipid Research,* 33, 1731-1740,
Chomczynski and Sacchi (1987) *Anal. Biochem,* 162, 156-159,
Choo et al. (1988) Proc. Natl. Acad. Sci. USA, 88, 2451-2455,
Choo et al. (1989) *Science,* 244, 359-362,
Feinstone et al. (1975) *N. Engl. J. Med,* 292, 767-770,
Feinstone et al. (1981) *J. Infect. Dis.,* 144, 588-598,
Fourmillier et al. (1996) *J. Gen. Virol.,* 77, 1055-1064,
Frese et al. (1995) *J. Virol.,* 69, 3904-3909,
Fuerst et al. (1986) *Proc. Natl. Acad. Sci. USA,* 83, 8122-8126,
Grakoui et al. (1993) *J. Virol.,* 67, 1385-1395,
Grakoui et al. (1993) *J. Virol.,* 67, 2832-2843,
Grakoui et al. (1993) *Proc. Natl. Acad. Sci. USA,* 90, 10583-10587,
Gübler U. and Hoffman B. J. (1983) *Gene,* 25, 263-269,
Hijikata et al. (1991) *Proc. Natl. Acad. Sci. USA,* 88, 5547-5551,
Inchauspé et al. (1991) *Proc. Natl. Acad. Sci. USA,* 88, 10292-10296,
Kato and Shimotohno (2000) *Curr Top Microbiol Immunol,* 242, 261-278,
Kato et al. (1990) *Proc. Natl. Acad. Sci. USA,* 87, 9524-9528,
Kieny et al. (1984) *Nature,* 312, 163-166,
Kolykhalov et al. (1997) *Science,* 277, 570-574,
Kowalski et al. (1976) *Biochemistry,* 15, 4457-4463,
Lanford et al. (1994) *Virology,* 202, 606-614,
Liljeström et al (1991) *J. Virol.,* 65, 4107-4113,
Lohmann et al. (1997) *Science,* 285, 110-113,
Moss et al. (1990) *Nature,* 348, 91-92,
Mullis, K. B. and Faloona F. A. (1987) *Meth. Enzymol.,* 155, 335-350,
Negro et al. (1992) *Proc. Natl. Acad. Sci. USA,* 1992, 89, 2247-2251,
Okamoto et al. (1992) *Virology,* 188, 331-341,
Prince et al. (1974) *Lancet,* 2, 241-246,
Reynolds et al. (1995) *The EMBO J,* 14, 6010-6020,
Seipp et al. (1997) *J. Gen. Virol.,* 2467-2476,
Shimizu et al. (1992) *Proc. Natl. Acad. Sci. USA,* 89, 5477-5481,
Shimizu et al. (1994) *J. Virol.,* 68, 1494-1500,
Shimizu et al. (1994) *J. Virol.,* 68, 8406-8408,
Simmonds P. (2001) *J. Gen. Virol.,* 82, 693-712,
Tsukiyama-Kohara et al. (1992) *J. Virol.,* 66, 1476-1483,
Wychowski et al. (1985), *Gene,* 37, 63-71,
Yanagi et al. (1997) *Proc. Natl. Acad. Sci. USA,* 94, 8738-8743,
Zarlenga and Gamble (1987) *Analytical Biochemistry,* 162, 569-574.

The invention claimed is:

1. An isolated nucleotide sequence characterized in that it comprises one of the following sequences: SEQ ID NO: 1 or SEQ ID NO: 3.

2. A recombinant vector containing a nucleotide sequence according to claim 1.

3. An isolated host cell selected from the group consisting of bacteria, cells used for viral production, yeasts, fungi, plants, and mammalian cells, said host cell being transformed using a recombinant vector according to claim 2.

4. The recombinant vector according to claim 2, wherein the vector is selected from the group consisting of a plasmid, a cosmid, a phage, and virus DNA.

* * * * *

SEQUENCE LISTING

```
<160> NUMBER OF SEQ ID NOS: 3

<210> SEQ ID NO 1
<211> LENGTH: 6609
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

ctggacacgg aggtggccgc gtcgtgtggc ggcgttgttc ttgtcgggtt aatggcgctg      60

actctgtcac catattacaa gcgctatatc agctggtgca tgtggtggct tcagtatttt     120

ctgaccagag tagaagcgca actgcacgtg tgggttcccc ccctcaacgt ccgggggggg     180

cgcgatgccg tcatcttact catgtgtgtt gtacacccga ctctggtatt tgacatcacc     240

aaactactcc tggccatctt cggacccctt tggattcttc aagccagttt gtttaaagtc     300

ccctacttcg tgcgcgttca aggccttctc cggatctgcg cgctagcgcg gaagatgacc     360

ggaggtcatt acgtgcaaat ggccatcatc aagttggggg cgcttactgg cacctatgtg     420

tataaccatc tcacccctct tcgagactgg gcgcacaacg gcctgcgaga tctggccgtg     480

gctgtggaac cagtcgtctt ctcccgaatg gagaccaagc tcatcacgtg gggggcagat     540
```

-continued accgccgcgt gcggtgacat catcaacggc ttgcccgtct ctgcccgtag gggccaggag 600
atactgcttg ggccagccga cggaatggtc tccaaggggt ggaggttgct ggcgcccatc 660
acggcgtacg cccagcagac gagaggcctc ctagggtgta taatcaccag cctgactggc 720
cgggacaaaa accaagtgga gggtgaggtc cagatcgtgt caactgctac ccaaaccttc 780
ctggcaacgt gcatcaatgg ggtatgctgg actgtctacc acggggccgg aacgaggacc 840
atcgcatcac ccaagggtcc tgtcatccag atgtatacca atgtggacca agaccttgtg 900
ggctggcccg ctcctcaagg ttcccgctca ttgacaccct gcacctgcgg ctcctcggac 960
ctttacctgg tcacgaggca cgccgacgtc attcccgtgc gccggcgagg tgatagcagg 1020
ggtagcctgc ttttgccccg gcccatttcc tacctaaaag gctcctcggg gggtccgctg 1080
ttgtgccccg cgggacacgc cgtgggccta ttcagggccg cggtgtgcac ccgtggagtg 1140
gccaaggcgg tggactttat ccctgtggag aacctagaga caaccatgag atccccggtg 1200
ttcacggaca actcctctcc accagcagtg ccccagagct tccaggtggc ccacctgcat 1260
gctcccaccg gcagtggtaa gagcaccaag gtcccggctg cgtacgcagc ccagggctac 1320
aaggtgttgg tgctcaaccc ctctgttgct gcaacgctgg gctttggtgc ttacatgtcc 1380
aaggcccatg gggtcgatcc taatatcagg accggggtga gaacaattac cactggcagc 1440
cccatcacgt actccaccta cggcaagttc cttgccgacg gcgggtgctc aggaggcgct 1500
tatgacataa taatttgtga cgagtgccac tccacggatg ccacatccat cttgggcatc 1560
ggcactgtcc ttgaccaagc agagactgcg gggggcgagat tggttgtgct cgccactgct 1620
acccctccgg gctccgtcac tgtgtcccat cctaacatcg aggaggttgc tctgtccacc 1680
accggagaga tccctttcta cggcaaggct atcccccctcg aggtgatcaa gggggggaaga 1740 catctcatct tctgtcactc aaagaagaag tgcgacgagc tcgccgcgaa gctggtcgca 1800
ttgggcatca atgccgtggc ctactaccgc ggacttgacg tgtctgtcat cccgaccagc 1860
ggcgatgttg tcgtcgtgtc gaccgatgct ctcatgactg gctttaccgg cgacttcgac 1920
tctgtgatag actgcaacac gtgtgtcact cagacagtcg atttcagcct tgaccctacc 1980
tttaccattg agacaaccac gctcccccag gatgctgtct ccaggactca gcgccggggc 2040
aggactggca gggggaagcc aggcatctac agatttgtgg caccggggga gcgcccctcc 2100
ggcatgttcg actcgtccgt cctctgtgag tgctatgacg cgggctgtgc ttggtatgag 2160
ctcatgcccg ccgagactac agttaggcta cgagcgtaca tgaacacccc ggggcttccc 2220
gtgtgccagg accatcttga attttgggag ggcgtcttta cgggcctcac ccatatagat 2280
gcccactttc tatcccagac aaagcagagt ggggagaact ttccttacct ggtagcgtac 2340
caagccaccg tgtgcgctag ggctcaagcc cctcccccat cgtgggacca gatgtggaag 2400
tgtttgatcc gccttaaacc caccctccat gggccaacac ccctgctata cagactgggc 2460
gctgttcaga atgaagtcac cctgacgcac ccaatcacca aatacatcat gacatgcatg 2520
tcggccgacc tggaggtcgt cacgagcacc tgggtgctcg ttggcggcgt cctggctgct 2580
ctggccgcgt attgcctgtc aacaggctgc gtggtcatag tgggcaggat tgtcttgtcc 2640
gggaagccgg caattatacc tgacagggag gttctctacc aggagttcga tgagatggaa 2700
gagtgctctc agcacttacc gtacatcgag caagggatga tgctcgctga gcagttcaag 2760
cagaaggccc tcggcctcct gcagaccgcg tcccgccatg cagaggttat cacccctgct 2820
gtccagacca actggcagaa actcgaggtc ttctgggcga agcacatgtg gaatttcatc 2880
agtgggatac aatatttggc gggcctgtca acgctgcctg gtaaccccgc cattgcttca 2940

-continued

```
ttgatggctt ttacagctgc cgtcaccagc ccactaacca ctggccaaac cctcctcttc   3000
aacatattgg gggggtgggt ggctgcccag ctcgccgccc ccggtgccgc taccgccttt   3060
gtgggcgctg gcttagctgg cgccgccatc ggcagcgttg gactggggaa ggtcctcgtg   3120
gacattcttg cagggtatgg cgcgggcgtg gcgggagctc ttgtagcatt caagatcatg   3180
agcggtgagg tcccctccac ggaggacctg gtcaatctgc tacccgccat cctctcgcct   3240
ggagcccttg tagtcggtgt ggtctgcgca gcaatactgc gccggcacgt tggcccgggc   3300
gagggggcag tgcaatggat gaaccggcta atagccttcg cctcccgggg gaaccatgtt   3360
tcccccacgc actacgtgcc ggagagcgat gcagccgccc gcgtcactgc catactcagc   3420
agcctcactg taacccagct cctgaggcga ctacatcagt ggataagctc ggagtgtacc   3480
actccatgct ccggctcctg gctaagggac atctgggact ggatatgcga ggtgctgagc   3540
gactttaaga cctggctgaa agccaagctc atgccacaac tgcctgggat tccctttgtg   3600
tcctgccagc gcgggtatag gggggtctgg cgaggagacg gcattatgca cactcgctgc   3660
cactgtggag ctgagatcac tggacatgtc aaaaacggga cgatgaggat cgtcggtcct   3720
aggacctgca ggaacatgtg gagtgggacg ttccccatta acgcctacac cacgggcccc   3780
tgtactcccc ttcctgcgcc gaactataag ttcgcgctgt ggagggtgtc tgcagaggaa   3840
tacgtggaga taaggcgggt gggggacttc cactacgtat cgggtatgac tactgacaat   3900
cttaaatgcc cgtgccagat cccatcgccc gaatttttca cagaattgga cggggtgcgc   3960
ctacataggt ttgcgccccc ttgcaagccc ttgctgcggg aggaggtatc attcagagta   4020
ggactccacg agtacccggt ggggtcgcaa ttaccttgcg agcccgaacc ggacgtagcc   4080
gtgttgacgt ccatgctcac tgatccctcc catataacag cagaggcggc cgggagaagg   4140
ttggcgagag ggtcaccccc ttctatggcc agctcctcgg ccagccagct gtccgctcca   4200
tctctcaagg caacttgcac cgccaaccat gactcccctg acgccgagct catagaggct   4260
aacctcctgt ggaggcagga gatgggcggc aacatcacca gggttgagtc agagaacaaa   4320
gtggtgattc tggactcctt cgatccgctt gtggcagagg aggatgagcg ggaggtctcc   4380
gtacccgcag aaattctgcg gaagtctcgg agattcgccc gggccctgcc cgtttgggcg   4440
cggccggact acaacccccc gctagtagag acgtggaaaa agcctgacta cgaaccacct   4500
gtggtccatg gctgcccgct accacctcca cggtcccctc ctgtgcctcc gcctcggaaa   4560
aagcgtacgg tggtcctcac cgaatcaacc ctacctactg ccttggccga gcttgccacc   4620
aaaagttttg gcagctcctc aacttccggc attacgggcg acaatatgac aacatcctct   4680
gagcccgccc cttctggctg cccccccgac tccgacgttg agtcctattc ttccatgccc   4740
cccctggagg gggagcctgg ggatccggat ttcagcgacg ggtcatggtc gacggtcagt   4800
agtggggccg acacggaaga tgtcgtgtgc tgctcaatgt cttatacctg gacaggcgca   4860
ctcgtcaccc cgtgcgctgc ggaagaacaa aaactgccca tcaacgcact gagcaactcg   4920
ttgctacgcc atcacaatct ggtatattcc accacttcac gcagtgcttg ccaaaggcag   4980
aagaaagtca catttgacag actgcaagtt ctggacagcc attaccagga cgtgctcaag   5040
gaggtcaaag cagcggcgtc aaaagtgaag gctaacttgc tatccgtaga ggaagcttgc   5100
agcctgacgc ccccacattc agccaaatcc aagtttggct atggggcaaa agacgtccgt   5160
tgccatgcca gaaaggccgt agcccacatc aactccgtgt ggaaagacct tctggaagac   5220
agtgtaacac caatagacac tatcatcatg gccaagaacg aggtcttctg cgttcagcct   5280
```

-continued

```
gagaaggggg gtcgtaagcc agctcgtctc atcgtgttcc ccgacctggg cgtgcgcgtg   5340

tgcgagaaga tggccctgta cgacgtggtt agcaaactcc ccctggccgt gatgggaagc   5400

tcctacggat tccaatactc accaggacag cgggttgaat tcctcgtgca agcgtggaag   5460

tccaagaaga ccccgatggg gttcccgtat gatacccgct gttttgactc cacagtcact   5520

gagagcgaca tccgtacgga ggaggcaatt taccaatgtt gtgacctgga cccccaagcc   5580

cgcgtggcca tcaagtccct cactgagagg ctttatgttg gggccctct taccaattca   5640

agggggggaaa actgcggcta tcgcaggtgc cgcgcgagcg gcgtactgac aactagctgt   5700

ggtaacaccc tcacttgcta catcaaggcc cgggcagccc gtcgagccgc agggctccag   5760

gactgcacca tgctcgtgtg tggcgacgac ttagtcgtta tctgtgaaag tgcgggggtc   5820

caggaggacg cggcgagcct gagagccttt acggaggcta tgaccaggta ctccgccccc   5880

cccggggacc ccccacaacc agaatacgac ttggagctta taacatcatg ctcctccaac   5940

gtgtcagtcg cccacgacgg cgctggaaaa agggtctact accttacccg tgaccctaca   6000

acccccctcg cgagagccgc gtgggagaca gcaagacaca ctccagtcaa ttcctggcta   6060

ggcaacataa tcatgtttgc ccccacactg tgggcgagga tgatactgat gacccatttc   6120

tttagcgtcc tcatagccag ggatcagctt gaacaggctc ttaactgtga gatctacgca   6180

gcctgctact ccatagaacc actggatcta cctccaatca ttcaaagact ccatggcctc   6240

agcgcatttt cactccacag ttactctcca ggtgaagtca atagggtggc cgcatgcctc   6300

agaaaacttg gggtcccgcc cttgcgagct tggagacacc gggcccggag cgtccgcgct   6360

aggcttctgt ccaggggagg cagggctgcc atatgtggca agtacctctt caactgggca   6420

gtaagaacaa agctcaaact cactccaata gcggccgctg gccggctgga cttgtccggt   6480

tggttcacgg ctggctacag cgggggagac atttatcaca gcgtgtctca tgcccggccc   6540

cgctggttct ggttttgcct actcctgctc gctgcagggg taggcatcta cctcctcccc   6600

aaccggtga                                                           6609
```

<210> SEQ ID NO 2
<211> LENGTH: 9622
<212> TYPE: DNA
<213> ORGANISM: Hepatitis C virus

<400> SEQUENCE: 2

```
gccagccccc tgatgggggc gacactccac catagatcac tcccctgtga ggaactactg     60

tcttcacgca gaaagcgtct agccatggcg ttagtatgag tgtcgtgcag cctccaggac    120

ccccccctccc gggagagcca tagtggtctg cggaaccggt gagtacaccg gaattgccag    180

gacgaccggg tcctttcttg gataaacccg ctcaatgcct ggagatttgg gcgtgccccc    240

gcaagactgc tagccgagta gtgttgggtc gcgaaaggcc ttgtggtact gcctgatagg    300

gtgcttgcga gtgccccggg aggtctcgta gaccgtgcac catgagcacg aatcctaaac    360

ctcaaagaaa aaccaaacgt aacaccaacc gtcgcccaca ggacgtcgag ttcccgggtg    420

gcggtcagat cgttggtgga gtttacttgt tgccgcgcag gggccctaga ttgggtgtgc    480

gcgcgacgag gaagacttcc gagcggtcgc aacctcgtgg tagacgtcag cctatcccca    540

aggcacgtcg gcccgagggc aggacctggg ctcagcccgg gtacccttgg cccctctatg    600

gcaatgaggg ttgcgggtgg gcgggatggc tcctgtctcc ccgtggctct cggcctagct    660

ggggccccac agacccccgg cgtaggtcgc gcaatttggg taaggtcatc gataccctta    720

cgtgcggctt cgccgacctc atggggtaca taccgctcgt cggcgcccct cttggaggcg    780
```

-continued

```
ctgccagggc cctggcgcat ggcgtccggg ttctggaaga cggcgtgaac tatgcaacag    840
ggaaccttcc tggttgctct ttctctatct tccttctggc cctgctctct tgcctgactg    900
tgcccgcttc agcctaccaa gtgcgcaatt cctcggggct ttaccatgtc accaatgatt    960
gccctaattc gagtattgtg tacgaggcgg ccgatgccat cctgcacact ccggggtgtg   1020
tcccttgcgt tcgcgagggt aacgcctcga ggtgttgggt ggcggtgacc cccacggtgg   1080
ccaccaggga cggcaaactc cccacaacgc agcttcgacg tcatatcgat ctgcttgtcg   1140
ggagcgccac cctctgctca gccctctacg tgggggacct gtgcgggtct gtttttcttg   1200
ttggtcaact gtttaccttc tctcccaggc gccactggac gacgcaaagc tgcaattgtt   1260
ctatctatcc cggccatata acgggtcatc gcatggcatg ggatatgatg atgaactggt   1320
cccctacggc agcgttggtg gtagctcagc tgctccggat cccacaagcc atcatggaca   1380
tgatcgctgg tgctcactgg ggagtcctgg cgggcatagc gtatttctcc atggtgggga   1440
actgggcgaa ggtcctggta gtgctgctgc tatttgccgg cgtcgacgcg gaaacccacg   1500
tcaccggggg aagtgccggc cacaccacgg ctgggcttgt tggtctcctt acaccaggcg   1560
ccaagcagaa catccaactg atcaacacca acggcagttg gcacatcaat agcacggcct   1620
tgaactgcaa cgatagcctt accaccggct ggttagcagg gctcttctat cgccacaaat   1680
tcaactcttc aggctgtcct gagaggttgg ccagctgccg acgccttacc gattttgccc   1740
agggctgggg tcccatcagt tatgccaacg gaagcggcct tgacgaacgc ccctactgtt   1800
ggcactaccc tccaagacct tgtggcattg tgcccgcaaa gagcgtgtgt ggcccggtat   1860
attgcttcac tcccagcccc gtggtggtgg gaacgaccga caggtcgggc gcgcctacct   1920
acagctgggg tgcaaatgat acggatgtct tcgtccttaa caacaccagg ccaccgctgg   1980
gcaattggtt cggttgtacc tggatgaact caactggatt caccaaagtg tgcggagcgc   2040
ccccttgtgt catcggaggg gtgggcaaca acaccttgct ctgccccact gattgcttcc   2100
gcaaacatcc ggaagccaca tactctcggt gcggctccgg tccctggatt acacccaggt   2160
gcatggtcga ctacccgtat aggctttggc actatccttg tactatcaat tacaccatat   2220
tcaaagtcag gatgtacgtg ggaggggtcg agcacaggct ggaagcggcc tgcaactgga   2280
cgcggggcga acgctgtgat ctggaagaca gggacaggtc cgagctcagc ccattgctgc   2340
tgtccaccac acagtggcag gtccttccgt gttctttcac gaccctgcca gccttgtcca   2400
ccggcctcat ccacctccac cagaacattg tggacgtgca gtacttgtac ggggtggggt   2460
caagcatcgc gtcctgggcc attaagtggg agtacgtcgt tctcctgttc cttctgcttg   2520
cagacgcgcg cgtctgctcc tgcttgtgga tgatgttact catatcccaa gcggaggcgg   2580
ctttggagaa cctcgtaata ctcaatgcag catccctggc cgggacgcac ggtcttgtgt   2640
ccttcctcgt gttcttctgc tttgcgtggt atctgaaggg taggtgggtg cccggagcgg   2700
tctacgcctt ctacgggatg tggcctctcc tcctgctcct gctggcgttg cctcagcggg   2760
catacgcact ggacacggag gtggccgcgt cgtgtggcgg cgttgttctt gtcgggttaa   2820
tggcgctgac tctgtcacca tattacaagc gctatatcag ctggtgcatg tggtggcttc   2880
agtattttct gaccagagta gaagcgcaac tgcacgtgtg ggttcccccc ctcaacgtcc   2940
gggggggcg cgatgccgtc atcttactca tgtgtgttgt acacccgact ctggtatttg   3000
acatcaccaa actactcctg gccatcttcg gacccctttg gattcttcaa gccagtttgt   3060
ttaaagtccc ctacttcgtg cgcgttcaag gccttctccg gatctgcgcg ctagcgcgga   3120
```

-continued

```
agatgaccgg aggtcattac gtgcaaatgg ccatcatcaa gttgggggcg cttactggca   3180
cctatgtgta taaccatctc acccctcttc gagactgggc gcacaacggc ctgcgagatc   3240
tggccgtggc tgtggaacca gtcgtcttct cccgaatgga gaccaagctc atcacgtggg   3300
gggcagatac cgccgcgtgc ggtgacatca tcaacggctt gcccgtctct gcccgtaggg   3360
gccaggagat actgcttggg ccagccgacg gaatggtctc caaggggtgg aggttgctgg   3420
cgcccatcac ggcgtacgcc cagcagacga gaggcctcct agggtgtata atcaccagcc   3480
tgactggccg ggacaaaaac caagtggagg gtgaggtcca gatcgtgtca actgctaccc   3540
aaaccttcct ggcaacgtgc atcaatgggg tatgctggac tgtctaccac ggggccggaa   3600
cgaggaccat cgcatcaccc aagggtcctg tcatccagat gtataccaat gtggaccaag   3660
accttgtggg ctggcccgct cctcaaggtt cccgctcatt gacaccctgc acctgcggct   3720
cctcggacct ttacctggtc acgaggcacg ccgacgtcat tcccgtgcgc cggcgaggtg   3780
atagcagggg tagcctgctt ttgccccggc ccatttccta cctaaaaggc tcctcggggg   3840
gtccgctgtt gtgccccgcg ggacacgccg tgggcctatt cagggccgcg gtgtgcaccc   3900
gtggagtggc caaggcggtg gactttatcc ctgtggagaa cctagagaca accatgagat   3960
ccccggtgtt cacggacaac tcctctccac cagcagtgcc ccagagcttc caggtggccc   4020
acctgcatgc tcccaccggc agtggtaaga gcaccaaggt cccggctgcg tacgcagccc   4080
agggctacaa ggtgttggtg ctcaacccct ctgttgctgc aacgctgggc tttggtgctt   4140
acatgtccaa ggcccatggg gtcgatccta atatcaggac cggggtgaga acaattacca   4200
ctggcagccc catcacgtac tccacctacg gcaagttcct tgccgacggc gggtgctcag   4260
gaggcgctta tgacataata atttgtgacg agtgccactc cacggatgcc acatccatct   4320
tgggcatcgg cactgtcctt gaccaagcag agactgcggg ggcgagattg gttgtgctcg   4380
ccactgctac ccctccgggc tccgtcactg tgtcccatcc taacatcgag gaggttgctc   4440
tgtccaccac cggagagatc cctttctacg gcaaggctat cccccctcgag gtgatcaagg   4500
ggggaagaca tctcatcttc tgtcactcaa agaagaagtg cgacgagctc gccgcgaagc   4560
tggtcgcatt gggcatcaat gccgtggcct actaccgcgg acttgacgtg tctgtcatcc   4620
cgaccagcgg cgatgttgtc gtcgtgtcga ccgatgctct catgactggc tttaccggcg   4680
acttcgactc tgtgatagac tgcaacacgt gtgtcactca gacagtcgat ttcagccttg   4740
accctacctt taccattgag acaaccacgc tcccccagga tgctgtctcc aggactcagc   4800
gccggggcag gactggcagg gggaagccag gcatctacag atttgtggca ccgggggagc   4860
gcccctccgg catgttcgac tcgtccgtcc tctgtgagtg ctatgacgcg ggctgtgctt   4920
ggtatgagct catgcccgcc gagactacag ttaggctacg agcgtacatg aacacccccgg   4980
ggcttcccgt gtgccaggac catcttgaat tttgggaggg cgtctttacg ggcctcaccc   5040
atatagatgc ccactttcta tcccagacaa agcagagtgg ggagaacttt ccttacctgg   5100
tagcgtacca agccaccgtg tgcgctaggg ctcaagcccc tcccccatcg tgggaccaga   5160
tgtggaagtg tttgatccgc cttaaaccca ccctccatgg gccaacaccc ctgctataca   5220
gactgggcgc tgttcagaat gaagtcaccc tgacgcaccc aatcaccaaa tacatcatga   5280
catgcatgtc ggccgacctg gaggtcgtca cgagcacctg ggtgctcgtt ggcggcgtcc   5340
tggctgctct ggccgcgtat tgcctgtcaa caggctgcgt ggtcatagtg ggcaggattg   5400
tcttgtccgg gaagccggca attatacctg acagggaggt tctctaccag gagttcgatg   5460
agatggaaga gtgctctcag cacttaccgt acatcgagca agggatgatg ctcgctgagc   5520
```

-continued

```
agttcaagca gaaggccctc ggcctcctgc agaccgcgtc ccgccatgca gaggttatca   5580
cccctgctgt ccagaccaac tggcagaaac tcgaggtctt ctgggcgaag cacatgtgga   5640
atttcatcag tgggatacaa tatttggcgg gcctgtcaac gctgcctggt aaccccgcca   5700
ttgcttcatt gatggctttt acagctgccg tcaccagccc actaaccact ggccaaaccc   5760
tcctcttcaa catattgggg gggtgggtgg ctgcccagct cgccgccccc ggtgccgcta   5820
ccgcctttgt gggcgctggc ttagctggcg ccgccatcgg cagcgttgga ctggggaagg   5880
tcctcgtgga cattcttgca gggtatggcg cgggcgtggc gggagctctt gtagcattca   5940
agatcatgag cggtgaggtc ccctccacgg aggacctggt caatctgcta cccgccatcc   6000
tctcgcctgg agcccttgta gtcggtgtgg tctgcgcagc aatactgcgc cggcacgttg   6060
gcccgggcga gggggcagtg caatggatga accggctaat agccttcgcc tcccggggga   6120
accatgtttc ccccacgcac tacgtgccgg agagcgatgc agccgcccgc gtcactgcca   6180
tactcagcag cctcactgta acccagctcc tgaggcgact acatcagtgg ataagctcgg   6240
agtgtaccac tccatgctcc ggctcctggc taagggacat ctgggactgg atatgcgagg   6300
tgctgagcga ctttaagacc tggctgaaag ccaagctcat gccacaactg cctgggattc   6360
cctttgtgtc ctgccagcgc gggtataggg gggtctggcg aggagacggc attatgcaca   6420
ctcgctgcca ctgtggagct gagatcactg gacatgtcaa aaacgggacg atgaggatcg   6480
tcggtcctag gacctgcagg aacatgtgga gtgggacgtt ccccattaac gcctacacca   6540
cgggcccctg tactcccctt cctgcgccga actataagtt cgcgctgtgg agggtgtctg   6600
cagaggaata cgtggagata aggcgggtgg gggacttcca ctacgtatcg ggtatgacta   6660
ctgacaatct taaatgcccg tgccagatcc catcgcccga atttttcaca gaattggacg   6720
gggtgcgcct acataggttt gcgccccctt gcaagccctt gctgcgggag gaggtatcat   6780
tcagagtagg actccacgag tacccggtgg ggtcgcaatt accttgcgag cccgaaccgg   6840
acgtagccgt gttgacgtcc atgctcactg atccctccca tataacagca gaggcggccg   6900
ggagaaggtt ggcgagaggg tcaccccctt ctatggccag ctcctcggcc agccagctgt   6960
ccgctccatc tctcaaggca acttgcaccg ccaaccatga ctcccctgac gccgagctca   7020
tagaggctaa cctcctgtgg aggcaggaga tgggcggcaa catcaccagg gttgagtcag   7080
agaacaaagt ggtgattctg gactccttcg atccgcttgt ggcagaggag gatgagcggg   7140
aggtctccgt acccgcagaa attctgcgga agtctcggag attcgcccgg gccctgcccg   7200
tttgggcgcg gccggactac aaccccccgc tagtagagac gtggaaaaag cctgactacg   7260
aaccacctgt ggtccatggc tgcccgctac cacctccacg gtcccctcct gtgcctccgc   7320
ctcggaaaaa gcgtacggtg gtcctcaccg aatcaaccct acctactgcc ttggccgagc   7380
ttgccaccaa aagttttggc agctcctcaa cttccggcat tacgggcgac aatatgacaa   7440
catcctctga gcccgcccct tctggctgcc cccccgactc cgacgttgag tcctattctt   7500
ccatgccccc cctggagggg gagcctgggg atccggattt cagcgacggg tcatggtcga   7560
cggtcagtag tggggccgac acggaagatg tcgtgtgctg ctcaatgtct tatacctgga   7620
caggcgcact cgtcaccccg tgcgctgcgg aagaacaaaa actgcccatc aacgcactga   7680
gcaactcgtt gctacgccat cacaatctgg tatattccac cacttcacgc agtgcttgcc   7740
aaaggcagaa gaaagtcaca tttgacagac tgcaagttct ggacagccat taccaggacg   7800
tgctcaagga ggtcaaagca gcggcgtcaa aagtgaaggc taacttgcta tccgtagagg   7860
```

-continued

```
aagcttgcag cctgacgccc ccacattcag ccaaatccaa gtttggctat ggggcaaaag   7920

acgtccgttg ccatgccaga aaggccgtag cccacatcaa ctccgtgtgg aaagaccttc   7980

tggaagacag tgtaacacca atagacacta tcatcatggc caagaacgag gtcttctgcg   8040

ttcagcctga gaagggggt cgtaagccag ctcgtctcat cgtgttcccc gacctgggcg    8100

tgcgcgtgtg cgagaagatg gccctgtacg acgtggttag caaactcccc ctggccgtga   8160

tgggaagctc ctacggattc caatactcac caggacagcg ggttgaattc ctcgtgcaag   8220

cgtggaagtc caagaagacc ccgatggggt tcccgtatga tacccgctgt tttgactcca   8280

cagtcactga gagcgacatc cgtacggagg aggcaattta ccaatgttgt gacctggacc   8340

cccaagcccg cgtggccatc aagtccctca ctgagaggct ttatgttggg ggccctctta   8400

ccaattcaag gggggaaaac tgcggctatc gcaggtgccg cgcgagcggc gtactgacaa   8460

ctagctgtgg taacaccctc acttgctaca tcaaggcccg ggcagcccgt cgagccgcag   8520

ggctccagga ctgcaccatg ctcgtgtgtg gcgacgactt agtcgttatc tgtgaaagtg   8580

cgggggtcca ggaggacgcg gcgagcctga gagcctttac ggaggctatg accaggtact   8640

ccgccccccc cggggacccc ccacaaccag aatacgactt ggagcttata acatcatgct   8700

cctccaacgt gtcagtcgcc cacgacggcg ctggaaaaag ggtctactac cttacccgtg   8760

accctacaac ccccctcgcg agagccgcgt gggagacagc aagacacact ccagtcaatt   8820

cctggctagg caacataatc atgtttgccc ccacactgtg ggcgaggatg atactgatga   8880

cccatttctt tagcgtcctc atagccaggg atcagcttga acaggctctt aactgtgaga   8940

tctacgcagc ctgctactcc atagaaccac tggatctacc tccaatcatt caaagactcc   9000

atggcctcag cgcattttca ctccacagtt actctccagg tgaagtcaat agggtggccg   9060

catgcctcag aaaacttggg gtcccgccct tgcgagcttg gagacaccgg gcccggagcg   9120

tccgcgctag gcttctgtcc aggggaggca gggctgccat atgtggcaag tacctcttca   9180

actgggcagt aagaacaaag ctcaaactca ctccaatagc ggccgctggc cggctggact   9240

tgtccggttg gttcacggct ggctacagcg gggagacat ttatcacagc gtgtctcatg    9300

cccggccccg ctggttctgg ttttgcctac tcctgctcgc tgcaggggta ggcatctacc   9360

tcctccccaa ccggtgaagg ttggggtaaa cactccggcc tcttaggcca tttccctttt   9420

ttttttttt ttttttttc cctttttttt tttttttttt ttttttttt ttttttttt       9480

tccttttcct tcttttttcc ctttctcttc ctcccttctt taatggtggc tccatcttag   9540

ccctagtcac ggctagctgt gaaaggtccg tgagccgcat gactgcagag agtgctgata   9600

ctggcctctc tgcagatcat gt                                            9622
```

<210> SEQ ID NO 3
<211> LENGTH: 8451
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 3

```
gccagccccc tgatgggggc gacactccac catagatcac tcccctgtga ggaactactg     60

tcttcacgca gaaagcgtct agccatggcg ttagtatgag tgtcgtgcag cctccaggac    120

ccccccctccc gggagagcca tagtggtctg cggaaccggt gagtacaccg gaattgccag   180

gacgaccggg tcctttcttg gataaacccg ctcaatgcct ggagatttgg gcgtgccccc    240
```

-continued

```
gcaagactgc tagccgagta gtgttgggtc gcgaaaggcc ttgtggtact gcctgatagg    300

gtgcttgcga gtgccccggg aggtctcgta gaccgtgcac catgagcacg aatcctaaac    360

ctcaaagaaa aaccaaacgt aacaccaacc gtcgcccaca ggacgtcgag ttcccgggtg    420

gcggtcagat cgttggtgga gtttacttgt tgccgcgcag gggccctaga ttgggtgtgc    480

gcgcgacgag gaagacttcc gagcggtcgc aacctcgtgg tagacgtcag cctatcccca    540

aggcacgtcg gcccgagggc aggacctggg ctcagcccgg gtaccctatg aaaaagcctg    600

aactcaccgc gacgtctgtc gagaagtttc tgatcgaaaa gttcgacagc gtctccgacc    660

tgatgcagct ctcggagggc gaagaatctc gtgctttcag cttcgatgta ggagggcgtg    720

gatatgtcct gcgggtaaat agctgcgccg atggtttcta caaagatcgt tatgtttatc    780

ggcactttgc atcggccgcg ctcccgattc cggaagtgct tgacattggg gaattcagcg    840

agagcctgac ctattgcatc tcccgccgtg cacagggtgt cacgttgcaa gacctgcctg    900

aaaccgaact gcccgctgtt ctgcagccgg tcgcggaggc catggatgcg atcgctgcgg    960

ccgatcttag ccagacgagc gggttcggcc cattcggacc gcaaggaatc ggtcaataca   1020

ctacatggcg tgatttcata tgcgcgattg ctgatcccca tgtgtatcac tggcaaactg   1080

tgatggacga caccgtcagt gcgtccgtcg cgcaggctct cgatgagctg atgctttggg   1140

ccgaggactg ccccgaagtc cggcacctcg tgcacgcgga tttcggctcc aacaatgtcc   1200

tgacggacaa tggccgcata acagcggtca ttgactggag cgaggcgatg ttcggggatt   1260

cccaatacga ggtcgccaac atcttcttct ggaggccgtg gttggcttgt atggagcagc   1320

agacgcgcta cttcgagcgg aggcatccgg agcttgcagg atcgccgcgg ctccgggcgt   1380

atatgctccg cattggtctt gaccaactct atcagagctt ggttgacggc aatttcgatg   1440

atgcagcttg ggcgcagggt cgatgcgacg caatcgtccg atccggagcc gggactgtcg   1500

ggcgtacaca aatcgcccgc agaagcgcgg ccgtctggac cgatggctgt gtagaagtac   1560

tcgccgatag tggaaaccga cgccccagca ctcgtgggga tcgggagatg ggggaggcta   1620

actctagtct ggacacggag gtggccgcgt cgtgtggcgg cgttgttctt gtcgggttaa   1680

tggcgctgac tctgtcacca tattacaagc gctatatcag ctggtgcatg tggtggcttc   1740

agtattttct gaccagagta gaagcgcaac tgcacgtgtg ggttcccccc ctcaacgtcc   1800

gggggggcg cgatgccgtc atcttactca tgtgtgttgt acacccgact ctggtatttg   1860

acatcaccaa actactcctg gccatcttcg gacccctttg gattcttcaa gccagtttgt   1920

ttaaagtccc ctacttcgtg cgcgttcaag gccttctccg gatctgcgcg ctagcgcgga   1980

agatgaccgg aggtcattac gtgcaaatgg ccatcatcaa gttgggggcg cttactggca   2040

cctatgtgta taaccatctc acccctcttc gagactgggc gcacaacggc ctgcgagatc   2100

tggccgtggc tgtggaacca gtcgtcttct cccgaatgga gaccaagctc atcacgtggg   2160

gggcagatac cgccgcgtgc ggtgacatca tcaacggctt gcccgtctct gcccgtaggg   2220

gccaggagat actgcttggg ccagccgacg gaatggtctc caaggggtgg aggttgctgg   2280

cgcccatcac ggcgtacgcc cagcagacga gaggcctcct agggtgtata atcaccagcc   2340

tgactggccg ggacaaaaac caagtggagg gtgaggtcca gatcgtgtca actgctaccc   2400

aaaccttcct ggcaacgtgc atcaatgggg tatgctggac tgtctaccac ggggccggaa   2460

cgaggaccat cgcatcaccc aagggtcctg tcatccagat gtataccaat gtggaccaag   2520

accttgtggg ctggcccgct cctcaaggtt cccgctcatt gacaccctgc acctgcggct   2580

cctcggacct ttacctggtc acgaggcacg ccgacgtcat tcccgtgcgc cggcgaggtg   2640
```

-continued

```
atagcagggg tagcctgctt ttgccccggc ccatttccta cctaaaaggc tcctcggggg   2700
gtccgctgtt gtgccccgcg ggacacgccg tgggcctatt cagggccgcg gtgtgcaccc   2760
gtggagtggc caaggcggtg gactttatcc ctgtggagaa cctagagaca accatgagat   2820
ccccggtgtt cacggacaac tcctctccac cagcagtgcc ccagagcttc caggtggccc   2880
acctgcatgc tcccaccggc agtggtaaga gcaccaaggt cccggctgcg tacgcagccc   2940
agggctacaa ggtgttggtg ctcaacccct ctgttgctgc aacgctgggc tttggtgctt   3000
acatgtccaa ggcccatggg gtcgatccta atatcaggac cggggtgaga acaattacca   3060
ctggcagccc catcacgtac tccacctacg gcaagttcct tgccgacggc gggtgctcag   3120
gaggcgctta tgacataata atttgtgacg agtgccactc cacggatgcc acatccatct   3180
tgggcatcgg cactgtcctt gaccaagcag agactgcggg ggcgagattg gttgtgctcg   3240
ccactgctac ccctccgggc tccgtcactg tgtcccatcc taacatcgag gaggttgctc   3300
tgtccaccac cggagagatc cctttctacg gcaaggctat cccccctcgag gtgatcaagg   3360
ggggaagaca tctcatcttc tgtcactcaa agaagaagtg cgacgagctc gccgcgaagc   3420
tggtcgcatt gggcatcaat gccgtggcct actaccgcgg acttgacgtg tctgtcatcc   3480
cgaccagcgg cgatgttgtc gtcgtgtcga ccgatgctct catgactggc tttaccggcg   3540
acttcgactc tgtgatagac tgcaacacgt gtgtcactca gacagtcgat ttcagccttg   3600
accctacctt taccattgag acaaccacgc tcccccagga tgctgtctcc aggactcagc   3660
gccggggcag gactggcagg gggaagccag gcatctacag atttgtggca ccgggggagc   3720
gcccctccgg catgttcgac tcgtccgtcc tctgtgagtg ctatgacgcg ggctgtgctt   3780
ggtatgagct catgcccgcc gagactacag ttaggctacg agcgtacatg aacaccccgg   3840
ggcttcccgt gtgccaggac catcttgaat tttgggaggg cgtctttacg ggcctcaccc   3900
atatagatgc ccactttcta tcccagacaa agcagagtgg ggagaacttt ccttacctgg   3960
tagcgtacca agccaccgtg tgcgctaggg ctcaagcccc tcccccatcg tgggaccaga   4020
tgtggaagtg tttgatccgc cttaaaccca ccctccatgg gccaacaccc ctgctataca   4080
gactgggcgc tgttcagaat gaagtcaccc tgacgcaccc aatcaccaaa tacatcatga   4140
catgcatgtc ggccgacctg gaggtcgtca cgagcacctg ggtgctcgtt ggcggcgtcc   4200
tggctgctct ggccgcgtat tgcctgtcaa caggctgcgt ggtcatagtg ggcaggattg   4260
tcttgtccgg gaagccggca attatacctg acagggaggt tctctaccag gagttcgatg   4320
agatggaaga gtgctctcag cacttaccgt acatcgagca agggatgatg ctcgctgagc   4380
agttcaagca gaaggccctc ggcctcctgc agaccgcgtc ccgccatgca gaggttatca   4440
cccctgctgt ccagaccaac tggcagaaac tcgaggtctt ctgggcgaag cacatgtgga   4500
atttcatcag tgggatacaa tatttggcgg gcctgtcaac gctgcctggt aaccccgcca   4560
ttgcttcatt gatggctttt acagctgccg tcaccagccc actaaccact ggccaaaccc   4620
tcctcttcaa catattgggg gggtgggtgg ctgcccagct cgccgccccc ggtgccgcta   4680
ccgcctttgt gggcgctggc ttagctggcg ccgccatcgg cagcgttgga ctggggaagg   4740
tcctcgtgga cattcttgca gggtatggcg cgggcgtggc gggagctctt gtagcattca   4800
agatcatgag cggtgaggtc ccctccacgg aggacctggt caatctgcta cccgccatcc   4860
tctcgcctgg agcccttgta gtcggtgtgg tctgcgcagc aatactgcgc cggcacgttg   4920
gcccgggcga gggggcagtg caatggatga accggctaat agccttcgcc tcccggggga   4980
```

-continued

```
accatgtttc ccccacgcac tacgtgccgg agagcgatgc agccgcccgc gtcactgcca   5040
tactcagcag cctcactgta acccagctcc tgaggcgact acatcagtgg ataagctcgg   5100
agtgtaccac tccatgctcc ggctcctggc taagggacat ctgggactgg atatgcgagg   5160
tgctgagcga ctttaagacc tggctgaaag ccaagctcat gccacaactg cctgggattc   5220
cctttgtgtc ctgccagcgc gggtataggg ggtctggcg aggagacggc attatgcaca    5280
ctcgctgcca ctgtggagct gagatcactg gacatgtcaa aaacgggacg atgaggatcg   5340
tcggtcctag gacctgcagg aacatgtgga gtgggacgtt ccccattaac gcctacacca   5400
cgggcccctg tactcccctt cctgcgccga actataagtt cgcgctgtgg agggtgtctg   5460
cagaggaata cgtggagata aggcgggtgg gggacttcca ctacgtatcg ggtatgacta   5520
ctgacaatct taaatgcccg tgccagatcc catcgcccga atttttcaca gaattggacg   5580
gggtgcgcct acataggttt gcgccccctt gcaagccctt gctgcgggag gaggtatcat   5640
tcagagtagg actccacgag tacccggtgg ggtcgcaatt accttgcgag cccgaaccgg   5700
acgtagccgt gttgacgtcc atgctcactg atccctccca tataacagca gaggcggccg   5760
ggagaaggtt ggcgagaggg tcaccccctt ctatggccag ctcctcggcc agccagctgt   5820
ccgctccatc tctcaaggca acttgcaccg ccaaccatga ctcccctgac gccgagctca   5880
tagaggctaa cctcctgtgg aggcaggaga tgggcggcaa catcaccagg gttgagtcag   5940
agaacaaagt ggtgattctg gactccttcg atccgcttgt ggcagaggag gatgagcggg   6000
aggtctccgt acccgcagaa attctgcgga agtctcggag attcgcccgg gccctgcccg   6060
tttgggcgcg gccggactac aaccccccgc tagtagagac gtggaaaaag cctgactacg   6120
aaccacctgt ggtccatggc tgcccgctac cacctccacg gtcccctcct gtgcctccgc   6180
ctcggaaaaa gcgtacggtg gtcctcaccg aatcaaccct acctactgcc ttggccgagc   6240
ttgccaccaa aagttttggc agctcctcaa cttccggcat tacgggcgac aatatgacaa   6300
catcctctga gcccgcccct tctggctgcc cccccgactc cgacgttgag tcctattctt   6360
ccatgccccc cctggagggg gagcctgggg atccggattt cagcgacggg tcatggtcga   6420
cggtcagtag tggggccgac acggaagatg tcgtgtgctg ctcaatgtct tatacctgga   6480
caggcgcact cgtcaccccg tgcgctgcgg aagaacaaaa actgcccatc aacgcactga   6540
gcaactcgtt gctacgccat cacaatctgg tatattccac cacttcacgc agtgcttgcc   6600
aaaggcagaa gaaagtcaca tttgacagac tgcaagttct ggacagccat taccaggacg   6660
tgctcaagga ggtcaaagca gcggcgtcaa aagtgaaggc taacttgcta tccgtagagg   6720
aagcttgcag cctgacgccc ccacattcag ccaaatccaa gtttggctat ggggcaaaag   6780
acgtccgttg ccatgccaga aaggccgtag cccacatcaa ctccgtgtgg aaagaccttc   6840
tggaagacag tgtaacacca atagacacta tcatcatggc caagaacgag gtcttctgcg   6900
ttcagcctga gaaggggggt cgtaagccag ctcgtctcat cgtgttcccc gacctgggcg   6960
tgcgcgtgtg cgagaagatg gccctgtacg acgtggttag caaactcccc ctggccgtga   7020
tgggaagctc ctacggattc caatactcac caggacagcg ggttgaattc ctcgtgcaag   7080
cgtggaagtc caagaagacc ccgatggggt tcccgtatga tacccgctgt tttgactcca   7140
cagtcactga gagcgacatc cgtacggagg aggcaattta ccaatgttgt gacctggacc   7200
cccaagcccg cgtggccatc aagtccctca ctgagaggct ttatgttggg ggccctctta   7260
ccaattcaag gggggaaaac tgcggctatc gcaggtgccg cgcgagcggc gtactgacaa   7320
ctagctgtgg taacaccctc acttgctaca tcaaggcccg ggcagcccgt cgagccgcag   7380
```

-continued

```
ggctccagga ctgcaccatg ctcgtgtgtg gcgacgactt agtcgttatc tgtgaaagtg   7440

cgggggtcca ggaggacgcg gcgagcctga gagcctttac ggaggctatg accaggtact   7500

ccgccccccc cggggacccc ccacaaccag aatacgactt ggagcttata acatcatgct   7560

cctccaacgt gtcagtcgcc cacgacggcg ctggaaaaag ggtctactac cttacccgtg   7620

accctacaac ccccctcgcg agagccgcgt gggagacagc aagacacact ccagtcaatt   7680

cctggctagg caacataatc atgtttgccc ccacactgtg ggcgaggatg atactgatga   7740

cccatttctt tagcgtcctc atagccaggg atcagcttga acaggctctt aactgtgaga   7800

tctacgcagc ctgctactcc atagaaccac tggatctacc tccaatcatt caaagactcc   7860

atggcctcag cgcattttca ctccacagtt actctccagg tgaagtcaat agggtggccg   7920

catgcctcag aaaacttggg gtcccgccct tgcgagcttg gagacaccgg gcccggagcg   7980

tccgcgctag gcttctgtcc aggggaggca gggctgccat atgtggcaag tacctcttca   8040

actgggcagt aagaacaaag ctcaaactca ctccaatagc ggccgctggc cggctggact   8100

tgtccggttg gttcacggct ggctacagcg ggggagacat ttatcacagc gtgtctcatg   8160

cccggccccg ctggttctgg ttttgcctac tcctgctcgc tgcaggggta ggcatctacc   8220

tcctccccaa ccggtgacat ttcccttttt tttttttttt tttttttcc cttttttttt   8280

tttttttttt tttttttttt tttttttttt ccttttcctt cttttttccc tttctcttcc   8340

tcccttcttt aatggtggct ccatcttagc cctagtcacg gctagctgtg aaaggtccgt   8400

gagccgcatg actgcagaga gtgctgatac tggcctctct gcagatcatg t            8451
```